United States Patent [19]
Cullis-Hill et al.

[11] Patent Number: 5,668,116
[45] Date of Patent: Sep. 16, 1997

[54] ANTI-INFLAMMATORY COMPOUNDS AND COMPOSITIONS

[75] Inventors: David Cullis-Hill, Bondi Junction; Peter Ghosh, Fairlight, both of Australia

[73] Assignee: Anthropharm Pty. Limited, Bondi Junction, Australia

[21] Appl. No.: 613,535

[22] Filed: Mar. 11, 1996

Related U.S. Application Data

[63] Continuation of Ser. No. 182,541, Jan. 18, 1994, abandoned, which is a continuation-in-part of Ser. No. 71,277, Jun. 4, 1993, abandoned, which is a division of Ser. No. 903,081, Jun. 10, 1992, Pat. No. 5,470,840, which is a division of Ser. No. 423,455, Sep. 19, 1989, Pat. No. 5,145,841.

[30] Foreign Application Priority Data

| Mar. 19, 1987 | [AU] | Australia | P10951 |
| Jun. 15, 1987 | [AU] | Australia | P12478 |
| Dec. 9, 1987 | [AU] | Australia | 915819 |

[51] Int. Cl.$^6$ ................................. A61K 31/70
[52] U.S. Cl. ................. 514/54; 514/56; 536/21; 536/55.1; 536/121
[58] Field of Search .............. 514/54, 56; 536/21, 536/55.1, 121

[56] References Cited

U.S. PATENT DOCUMENTS

| 1,950,100 | 3/1934 | Crandall, Jr. | 536/131 |
| 3,247,063 | 4/1966 | Pulver | 514/56 |
| 3,636,202 | 1/1972 | Klein | 514/56 |
| 3,719,665 | 3/1973 | Beaufour et al. | 260/234 |
| 4,465,666 | 8/1984 | Lukas et al. | 424/78.06 |
| 4,510,135 | 4/1985 | Teng | 514/56 |
| 4,524,066 | 6/1985 | Wolf | 514/23 |
| 4,623,539 | 11/1986 | Tunc | 424/78.01 |
| 4,654,327 | 3/1987 | Teng | 514/56 |
| 4,710,493 | 12/1987 | Landsberger | 514/56 |
| 4,713,373 | 12/1987 | Bayol et al. | 514/54 |
| 4,727,063 | 2/1988 | Naggi et al. | 514/56 |
| 4,736,024 | 4/1988 | Della Valle et al. | 536/55.3 |
| 4,746,504 | 5/1988 | Nimrod et al. | 424/1.73 |
| 4,973,580 | 11/1990 | Mascellani et al. | 514/54 |

FOREIGN PATENT DOCUMENTS

| 39929 | of 1968 | Australia . |
| A1 66 307 | of 1980 | Australia . |
| B 22582 | of 1983 | Australia . |
| B-30806(555747) | of 1984 | Australia . |
| 0022856 | 7/1984 | Australia . |
| A-55662 | of 1986 | Australia . |
| A-70540 | of 1987 | Australia . |
| 0 140781 | of 1985 | European Pat. Off. . |
| 0 239 335 | of 1987 | European Pat. Off. . |
| 47-13263 | of 1973 | Germany . |
| 0136 572 | of 1979 | Germany . |
| 45-156 | of 1970 | Japan . |
| 49-42486 | of 1974 | Japan . |
| 49-42485 | of 1974 | Japan . |
| 61-13-301 | of 1986 | Japan . |
| 61-130301 | 6/1986 | Japan . |
| 603 571 | of 1948 | United Kingdom . |
| 2080682 | of 1982 | United Kingdom . |
| 2080682 | 2/1982 | United Kingdom . |
| 89/12070 | of 1989 | WIPO . |
| WO8912070 | 12/1989 | WIPO . |

OTHER PUBLICATIONS

Nagasawa et al, Arch. Biochem, Biophysics. 150:451, 458 (1972).
Kobayashi et al. Chem Abstract, 92:15572m (1980).
Balt et al, Chem. Abstract, 98:156708w (1983).
De Bolster et al, Chem. Abstract, 98:156709x (1983).
Goodman & Gilman's The Pharmacological Basis of . . . , 7th Edition, pp. 1471–1480 (1985).
The Merck Index, 10th Ed. Windholz et al (eds.), (1983), p. 1025 #7001.

*Primary Examiner*—Elli Peselev
*Attorney, Agent, or Firm*—Nixon & Vanderhye

[57] ABSTRACT

A method for inactivating viruses which comprises the step of contacting the virus with an effective amount of a substantially pure divalent metal ion chelate of a polysulfate of xylan having glycosidically linked D-glucuronyl side chains with divalent metal ions chelated thereto wherein substantially all monovalent ions have been substituted by divalent metal ions, said divalent metal ions being selected from the group consisting of $Ca^{2+}$, $Mg^{2+}$, $Cu^{2+}$ and $Zn^{2+}$.

6 Claims, 21 Drawing Sheets

ANTI-INFLAMMATORY COMPOUNDS AND COMPOSITIONS

This is a Continuation of application Ser. No. 08/182,541, filed Jan. 18, 1994, now abandoned, which is a CIP of application Ser. No. 08/071,277, filed Jun. 4, 1993, now abandoned, which is a Division of application Ser. No. 07/903,081, filed 10 June 1992, now U.S. Pat. No. 5,470,840 which is Division of application Ser. No. 07/423,455, filed Sep. 19, 1989, now U.S. Pat. No. 5,145,841.

TECHNICAL FIELD

The present invention relates to compounds, compositions and methods for the treatment of arthritis and allied inflammatory conditions. More particularly the invention relates to novel metallo complexes of polysulphated polysaccharides, compositions including those compounds, compositions including any two of the compounds selected from hyaluronic acid or water soluble salts thereof, corticosteroids and compounds capable of maintaining the integrity of connective tissues, particularly joint articular cartilage and methods for treating arthritis and allied inflammatory conditions using these compounds and compositions.

BACKGROUND ART

Arthritis and other related inflammatory conditions are generally debilitating, painful diseases that affect the joints of a significant portion of the human and other animal populations. As a result of the wide spread occurrence of such diseases, considerable medical effort has been directed towards producing and identifying therapies that are able to at least relieve some of attendant pain, and produce regression of the malady.

As a result of this work, many compounds have been found to be useful in the treatment of such inflammatory. diseases with varying degrees of success being achieved in relieving the pain of the disease and the restoration of the affected Joints to normal function.

One of the earliest compounds to be used to treat inflammatory disease, which was found to have some effect in relieving pain, was salicylic acid. Unfortunately, this compound was found to be excessively irritating to the gastrointestinal tract. Accordingly, many derivatives of salicylic acid were evaluated for anti-inflammatory activity which resulted in the identification of aspirin as an effective and relatively safe anti-inflammatory compound.

Since the discovery of aspirin, many other compounds have been produced which are claimed to be more effective than aspirin. These include such compounds as the phenylacetic acids exemplified by ibuprofen and more recently identified compounds such as naproxen and sulindac. Strong anti-inflammatory potency has been achieved with the corticosteroids (e.g. hydrocortisone, dexamethasone, prednisolone, methyl prednisolone, betamethasone, paramethasone, and triamcinolone) as their water soluble and insoluble derivatives and these are also widely prescribed.

However, all of these prior art compounds and compositions whilst displaying satisfactory analgesic anti-inflammatory properties, in that they relieve Joint pain to a certain extent in most cases, any beneficial effect that they have in restoring Joint function is usually only transitory.

Furthermore, prolonged therapy with these prior art compounds and compositions while providing continuing pain relief for many sufferers can lead to breakdown and failure of connective tissues, particularly articular cartilage which in fact may exacerbate the problem. Examples of this phenomenon are described by: Newman and Ling, *Lancet* Jul. 6, 11–14, 1985; Watson, *Rheum. Rehab.*, 15, 26–30, 1976; McKenzie, Horsburgh, Ghosh and Taylor *Ann. Rheum. Dis.* 35, 487–417, 1976; Burkhardt and Ghosh, *Seminars in Arthritis and Rheumatism, Suppl.* 1, 17, 1–34, 1987. Corticosteroids, while still extensively used as anti-inflammatory agents for intra-articular treatment of severe arthropathies, are amongst the most potent inhibitors of connective tissue growth, repair and biosynthesis of matrix components (see Silbermana et al., *Bone and Mineral* 2, 87–106, 1987; Rimza, *AM. J. Dis. Child.* 132, 806–810, 1978; Canalis, *Endocrinology*, 112, 931–939, 1983; Reynolds, *Exp. Cell. Res.* 41, 174–189, 1966; Oikarinen, *Biochem. Pharmacol.* 26, 875–879, 1977, Silbermann et al., *Growth*, 47, 77–96, 1983, Saarni. *Biochem. Pharmacol*, 26, 1961–1966, 1977 Olah, and Kostenszky, *Acta. Biol. Acad. Sci. Hung.* 27, 129–134, 1976). Many clinical reports have appeared condemning the long term uses of these agents, reviewed by Neustadt, in "Osteoarthritis, Diagnosis and Management, Chapter 19, Eds. Moskowitz, Howell, Goldberg, Mankin, W. B. Saunders and Co. 1984).

In more recent times, considerable research has been conducted to elucidate the causative mechanism of arthritis and other inflammatory diseases. Included in this work has been investigations of the normal joint function and the recognition of pathological signs associated with the disease.

As a result of the aforementioned work, hyaluronate has been identified as one of the major non-protein components present in the synovial fluid of animal joints and it has been found to be largely responsible for the theological properties of synovial fluid, these properties being dependent on the concentration and molecular size of the hyaluronate. It should be noted that hyaluronate is a naturally occurring glycosaminoglycan present in many tissues, in addition to the synovial fluid, of the bodies of animals.

As a consequence of this latter finding, work has been directed towards determining the role of hyaluronate in normal joint function and the changes, if any, that occur in diseased joints. The findings of this latter work has led to the suggestion that application of hyaluronate, obtained from disease free tissues, to diseased joints may assist in restoring normal joint function and the relief of pain associated with the diseased joints.

However, it would appear that the results of such treatments in the past have been disappointing since the newly introduced hyaluronate is itself rapidly broken down by the inflammatory cells free radicals and their enzymes within the joint thereby losing its beneficial properties.

This finding also suggests that even if hyaluronate of the correct molecular size range was applied to diseased joints, it is likely that only temporary relief would result unless the hyaluronate was provided to the joint on a continuous basis.

Moreover, it has been found in vitro by the present inventors that hyaluronate synthesized by cells derived from arthritic synovial joints is of a smaller molecular size than that normally secreted. This finding suggests that to further restore normality of function the production of hyaluronate within the joints should be controlled to ensure that the hyaluronate produced is of the correct molecular size range.

In accordance with the finding of molecular size reduction of hyaluronate in diseased joints, as well as the rapid breakdown and loss of normal size by hyaluronate when introduced into the pathological joint, and the benefit to be gained by controlling the synthesis of hyaluronate of the correct molecular size range, the present inventors have surprisingly found that by combining hyaluronate with compounds which suppress the migration into the joint of inflammatory cells, the release by these cells of inflammatory mediators, free radicals and proteolytic enzymes, then the integrity and biosynthesis of the hyaluronate may be preserved.

DISCLOSURE OF INVENTION

The present invention consists in a first aspect in a composition for treating inflammatory joint diseases comprising a pharmaceutically acceptable carrier, and at least any two of the compounds selected from the group consisting of hyaluronic acid or water soluble salts thereof, corticosteroids and compounds capable of maintaining the integrity of connective tissues, particularly joint articular cartilage.

In a second aspect, the present invention further consists in a method for the treatment of inflammatory joint diseases, comprising administering to an affected joint, an effective amount of a composition comprising a pharmaceutically acceptable carrier, and at least any two of the compounds selected from the group consisting of hyaluronic acid or water soluble salts thereof, corticosteroids and compounds capable of maintaining the integrity of connective tissues, particularly joint articular cartilage.

In one embodiment, the inventive composition comprises a pharmaceutically acceptable carrier, hyaluronic acid or water soluble salts thereof, a corticosteroid and a compound capable of maintaining the integrity of connective tissues, particularly joint articular cartilage.

The advantage of the inventive composition and method are clear in that they offer the possibility of being able to effectively treat a range of inflammatory joint diseases.

Compounds of the invention which are capable of maintaining the integrity of connective tissues, particularly joint articular cartilage include polysulphated polysaccharides such as xylan polysulfate or Arteparon (registered trade mark of Luitpold GmbH for dextran sulphate).

The most preferred corticosteroids include hydrocortisone, prednisolone and triamcinolone as water soluble derivatives.

(■)=cartilage incubated alone (■)=cartilage+5×10$^4$ macrophage (▨)=cartilage+1:10 dilution of macrophage culture media In the DH40G group the experimental conditions were the same as controls but 200 ug/ml of drug was used.

Figure 12:
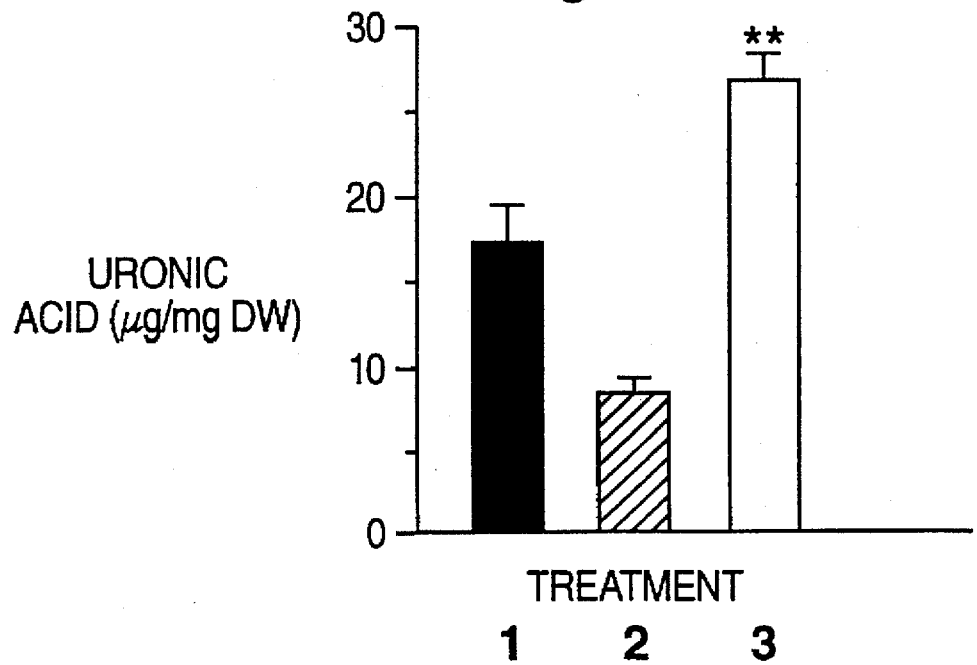

FIG. 12—Proteoglycan content (as determined by Uronic acid) of articular cartilages implanted in rat air pouches subjected to (1) physiological saline (■), (2) peptone (■), and (3) peptone+DH40J (□) treatment for seven days at 10 mg/kg/day. ** Indicates statistically different to non-drug treated group (2) (p<0.001).

Figure 4:
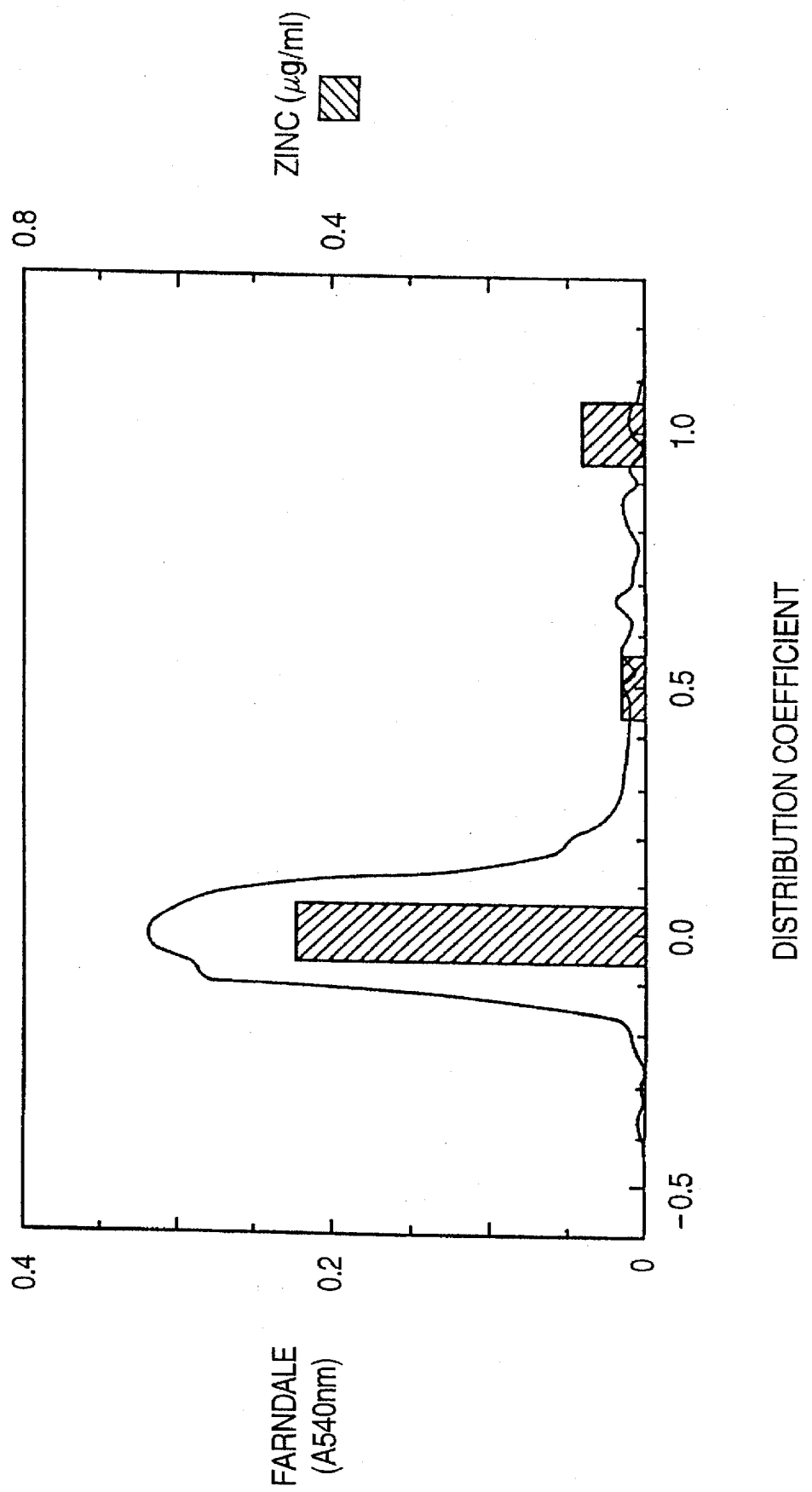
FIG. 4—Sephadex G-25 chromatography of DH40G using HEPES buffer (50 nM) at pH 7.0. Fractions were assayed for sulphated polysaccharides using the Farndale et. al. assay (Connective Tissue Research, 9, 247–249, 1982), Zn was determined by atomic absorption spectroscopy and is shown as ug/ml (■).
Figure 13:
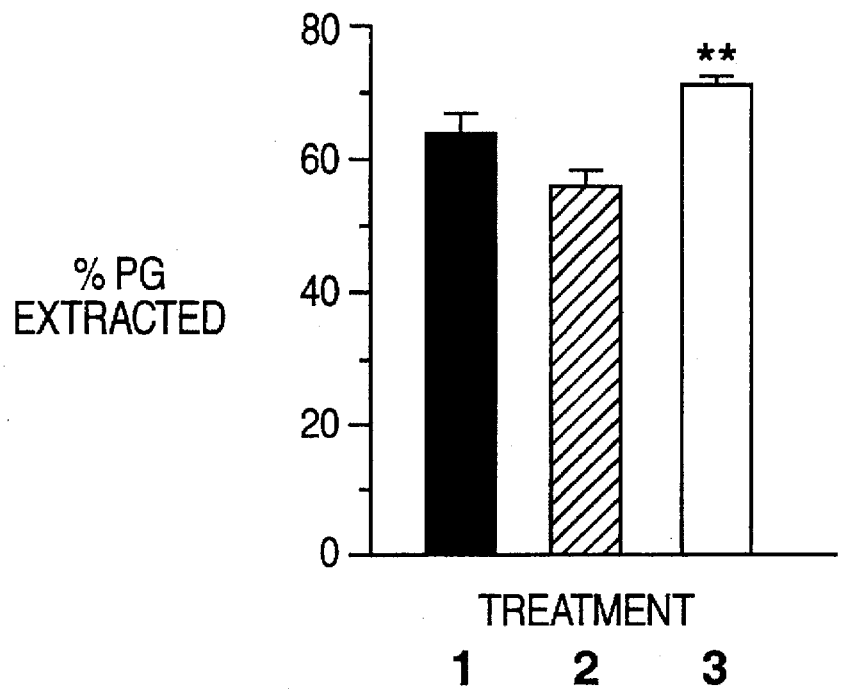

FIG. 13—4.0 M-GuHCl extractability of proteoglycans from articular cartilage removed from rat air pouches after treatment with (1) physiological saline (■), (2) peptone (■), and (3) peptone+DH40J (□) treatment at 10 mg/kg/day for seven days . ** Indicates statistically different to non-drug treated group.(2) (p<0.05).

Figure 14:
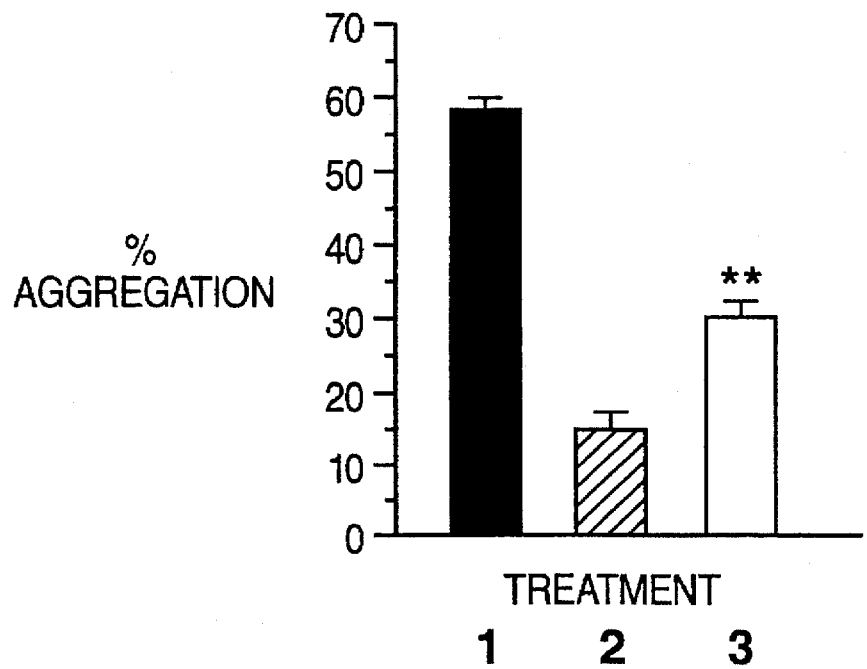

FIG. 14—Aggregation (as a % of total present) of proteoglycans extracted-from articular cartilages implanted in rat air pouch subjected to (1) physiological saline (■), (2) peptone (■), and (3) peptone+DH48J (□) treatment at 10 mg/kg/day for seven days. ** Indicates statistically different to non-drug treated group (2) (p<0.001).

Figure 15:
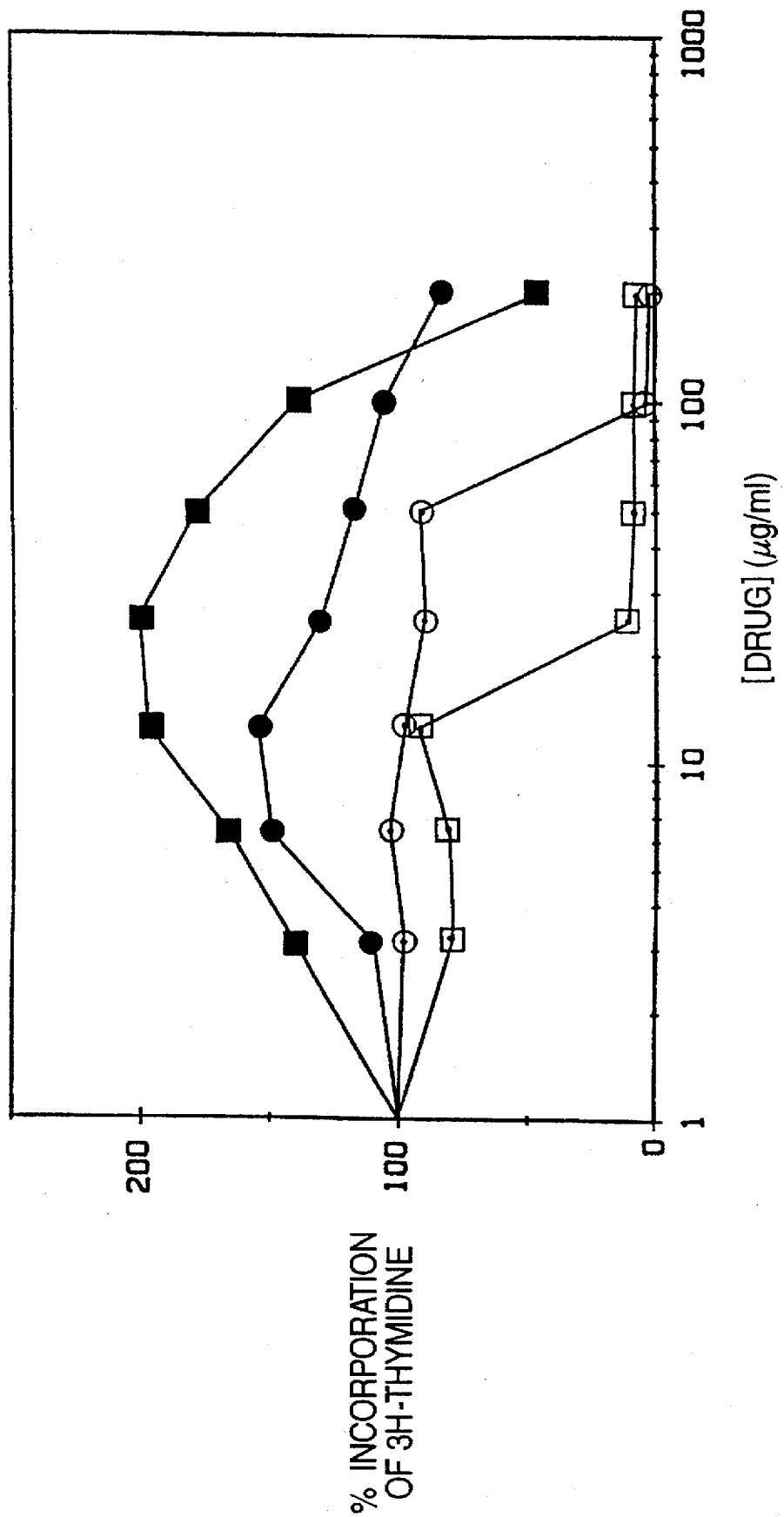

FIG. 15—Effects of Pentosan polysulphate (SP54®) (●), DH40J (■), ZnSO$_4$ (□) and SP54®+ZnSO$_4$ in the ratio of 1.0:0.2) (○) on DNA synthesis by a human synovial fibroblast line derived from synovium of an osteoarthritic joint.

Figure 16:
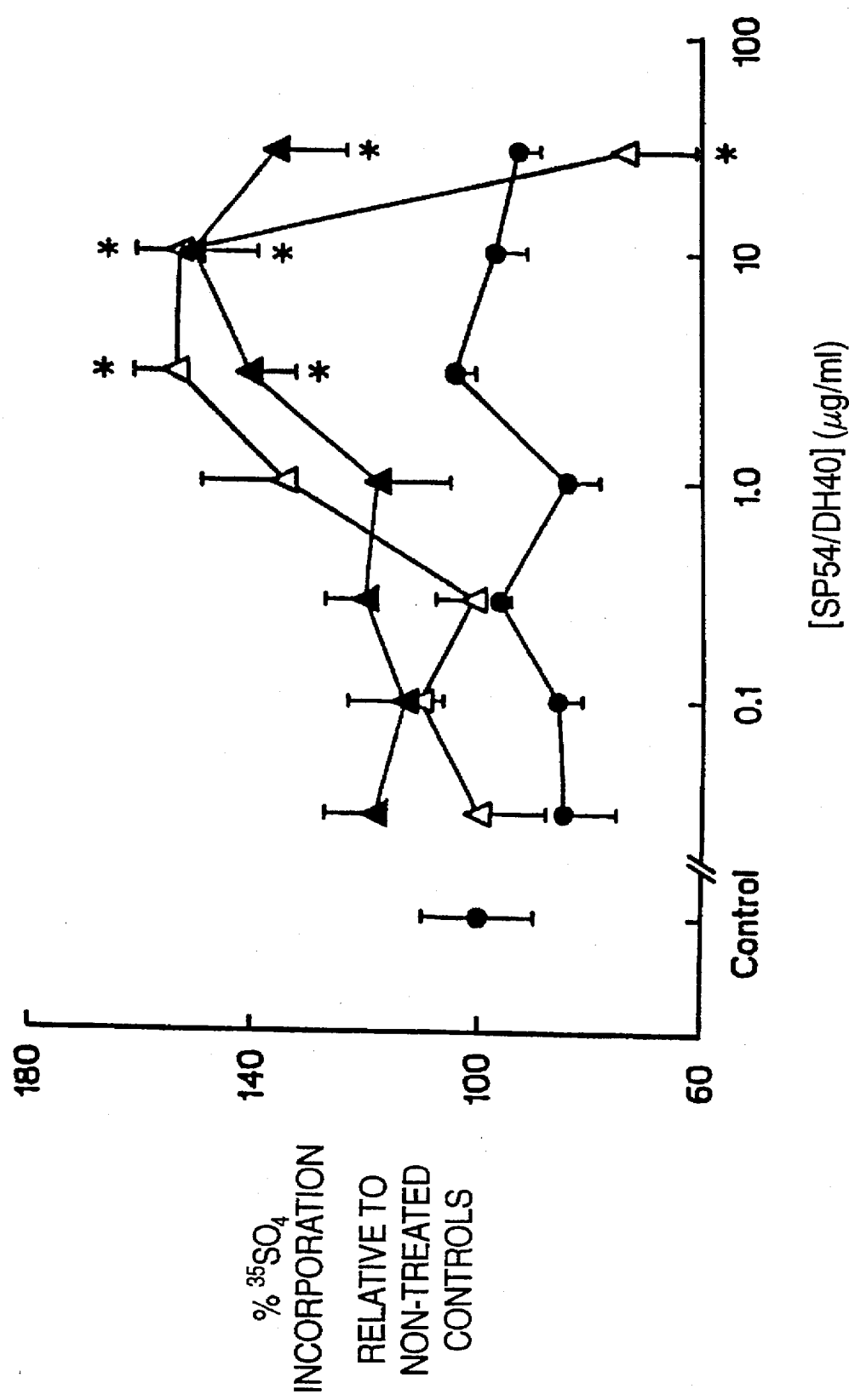

FIG. 16—Effects of Pentosan polysulphate (SP54®) (●), DH40J (▲) and DH40Y (Δ) on the in vitro synthesis of proteoglycans by rabbit articular chondrocytes. Vales shown are means±SD, n=4. * Indicates values statistically significantly different from SP54® (p<0.01).

Figure 17:
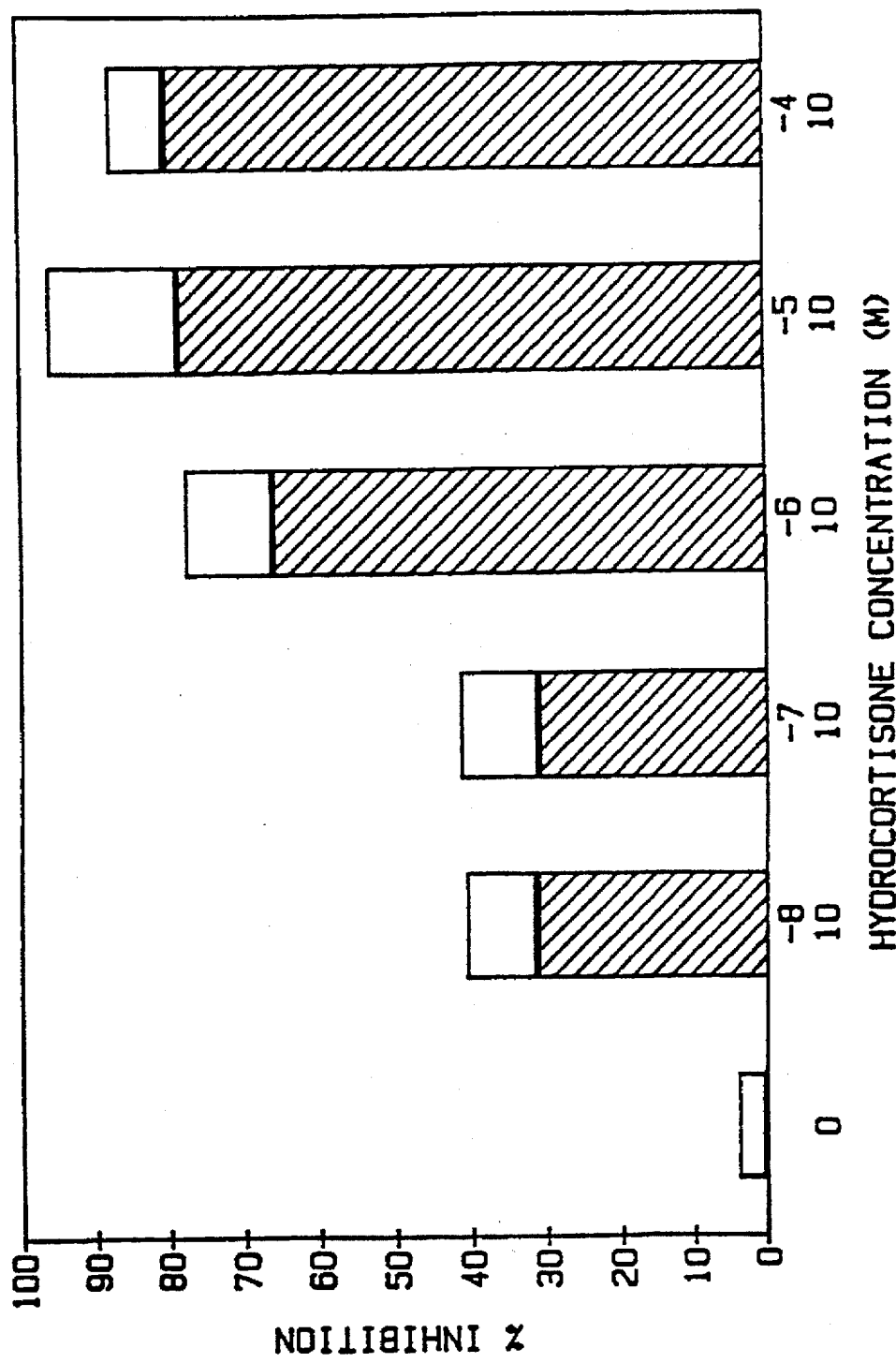

FIG. 17—Effects of hydrocortisone at various molar concentrations (M) on the in vitro biosynthesis of hyaluronic acid by a synovial fibroblast cell line derived from OA joint.

■=mean □=SD.

Figure 18:
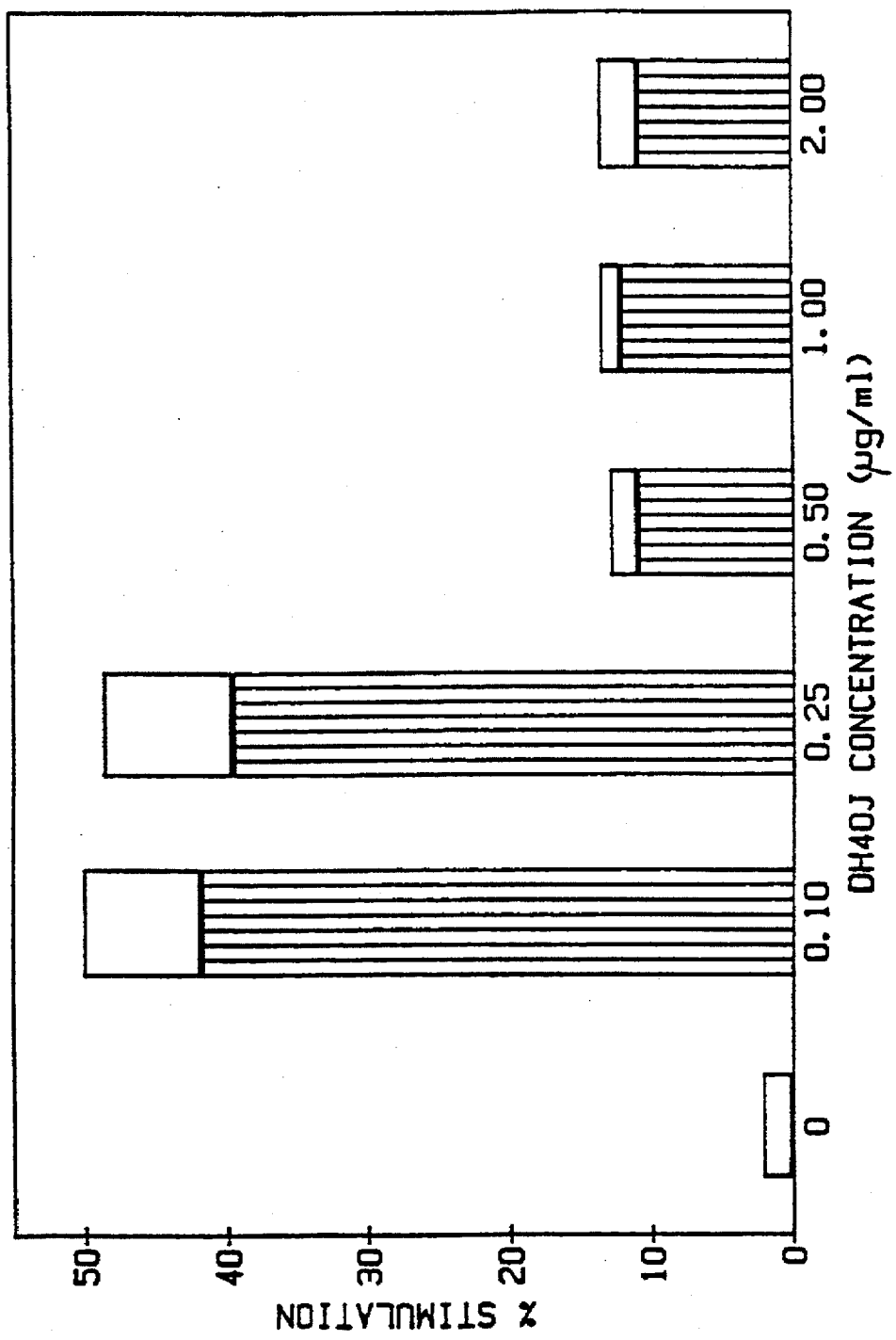

FIG. 18—Effects of various concentrations (ug/ml) of DH40J on the in vitro biosynthesis of hyaluronic acid by a synovial fibroblast line derived from OA joints.

▩=mean □=SD.

Note: at 0.10 ug/ml DH40J was approximately 2× more stimulatory than SP54® at the same concentration.

Figure 19:
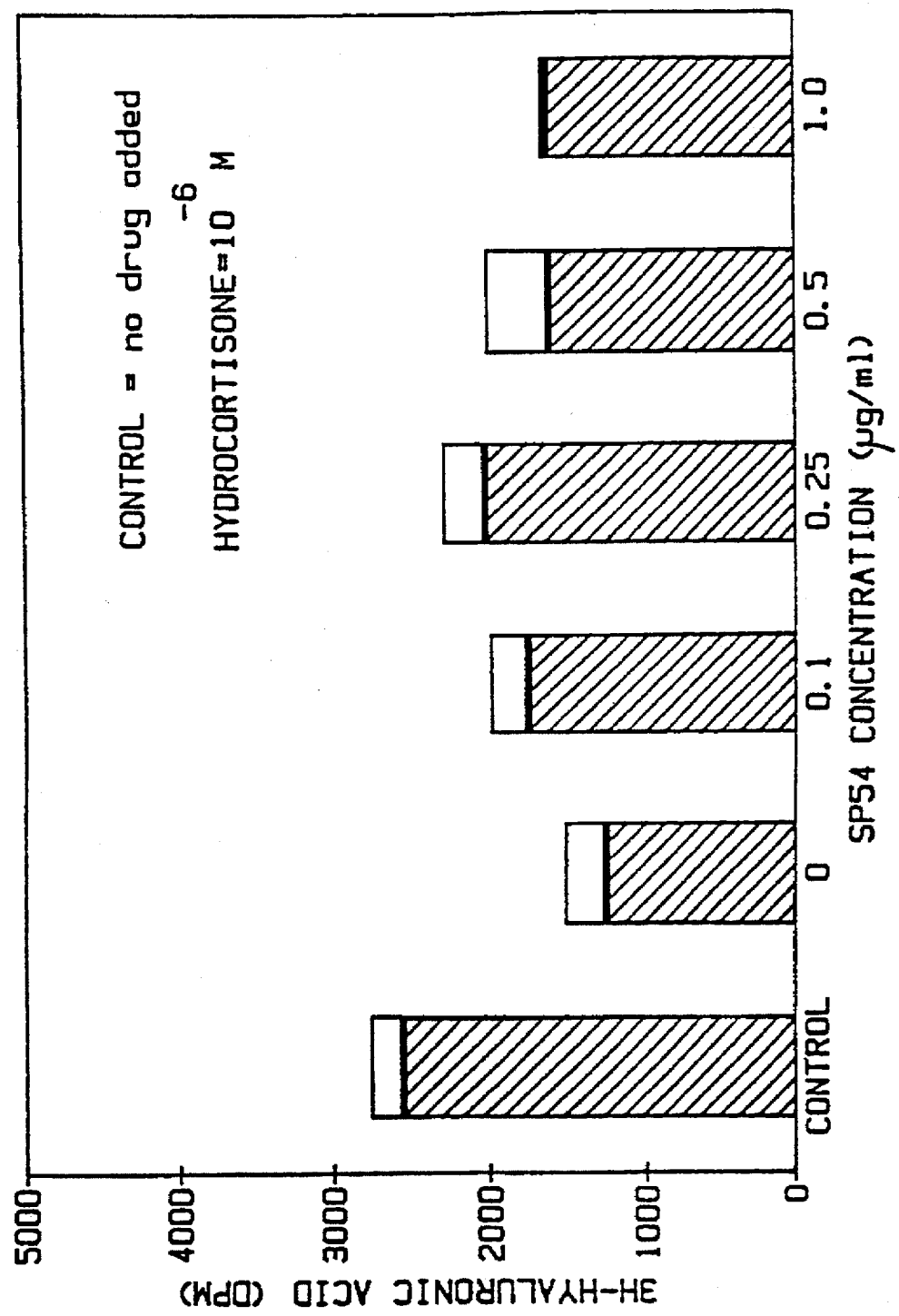

FIG. 19—Combined effects of hydrocortisone (at $10^6$M) and Pentosan polysulphate (SP54®) at various concentrations on the in vitro biosynthesis of hyaluronic acid by a synovial fibroblast line derived from OA joints.

■=mean □=SD

Note: at 0.25 ug/ml biosynthesis of HA suppressed by hydrocortisone was almost, but not totally, restored to control value.

Figure 20:
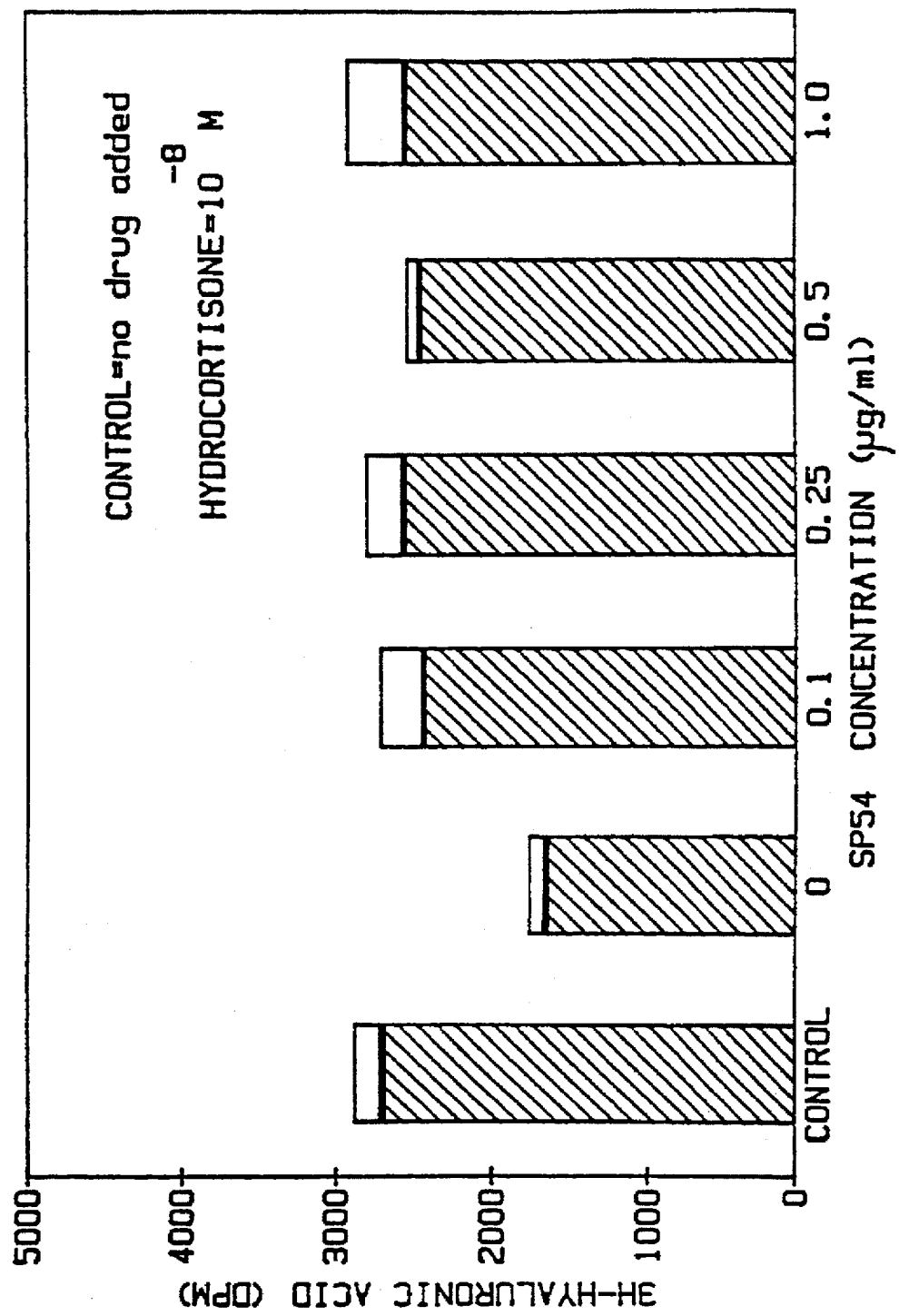

FIG. 20—Combined effects of hydrocortisone (at $10^8$M) and Pentosan polysulphate (SP54®) at various concentrations on the in vitro biosynthesis of hyaluronic acid by a synovial fibroblast line derived from OA joints.

■=mean □=SD

Note: that at concentrations between 0.1–1.0 ug/ml SP54® fully restored synthesis to control values even in the presence of hydrocortisone.

Figure 21:
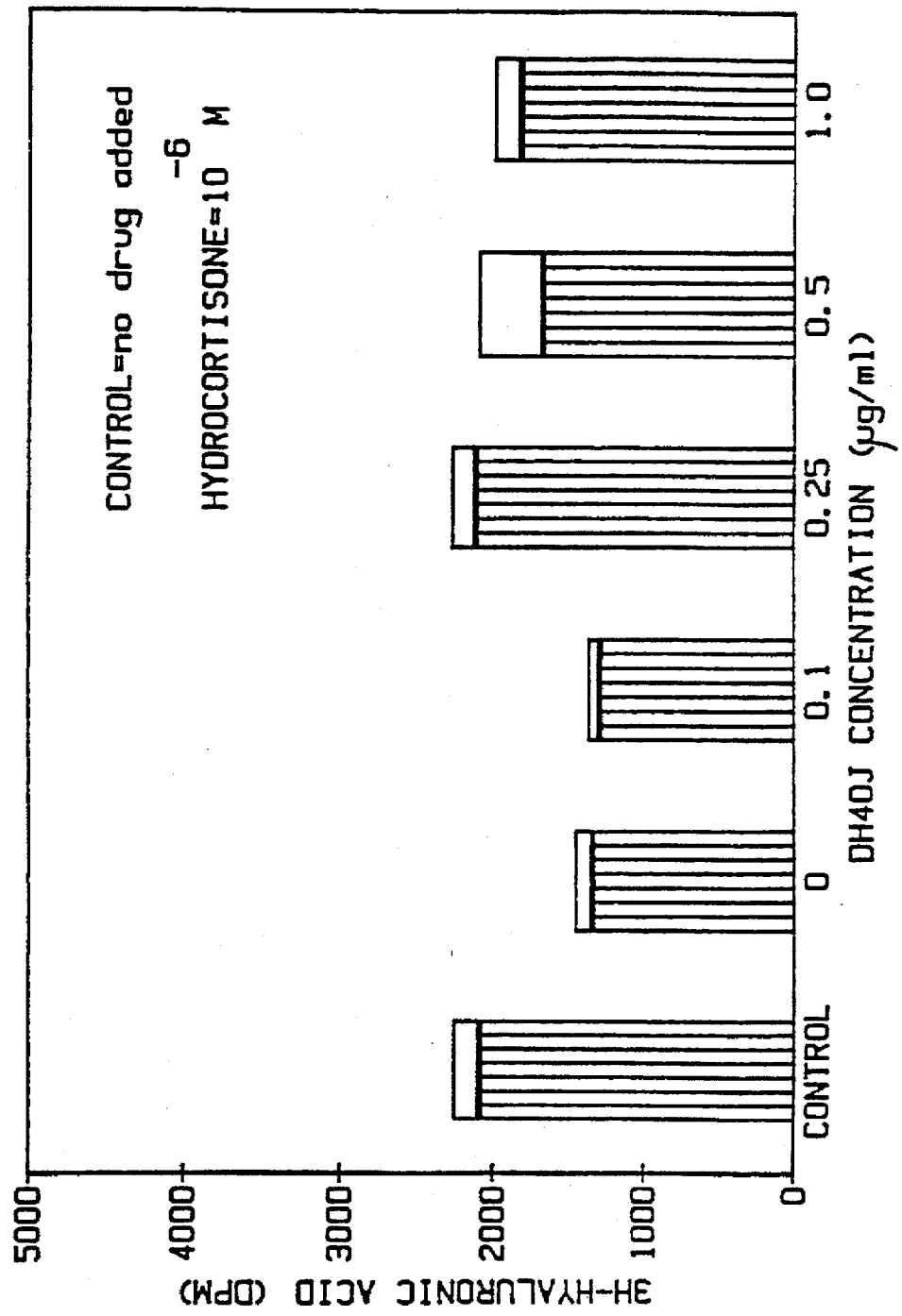

FIG. 21—Combined effects of hydrocortisone (at $10^6$M) and DH40J at various concentrations on the in vitro biosynthesis of hyaluronic acid (HA) by synovial fibroblasts derived from OA joints.

▩=mean □=SD

Note: at 0.25 ug/ml DH40J restored the biosynthesis of HA to normal values.

Figure 22:
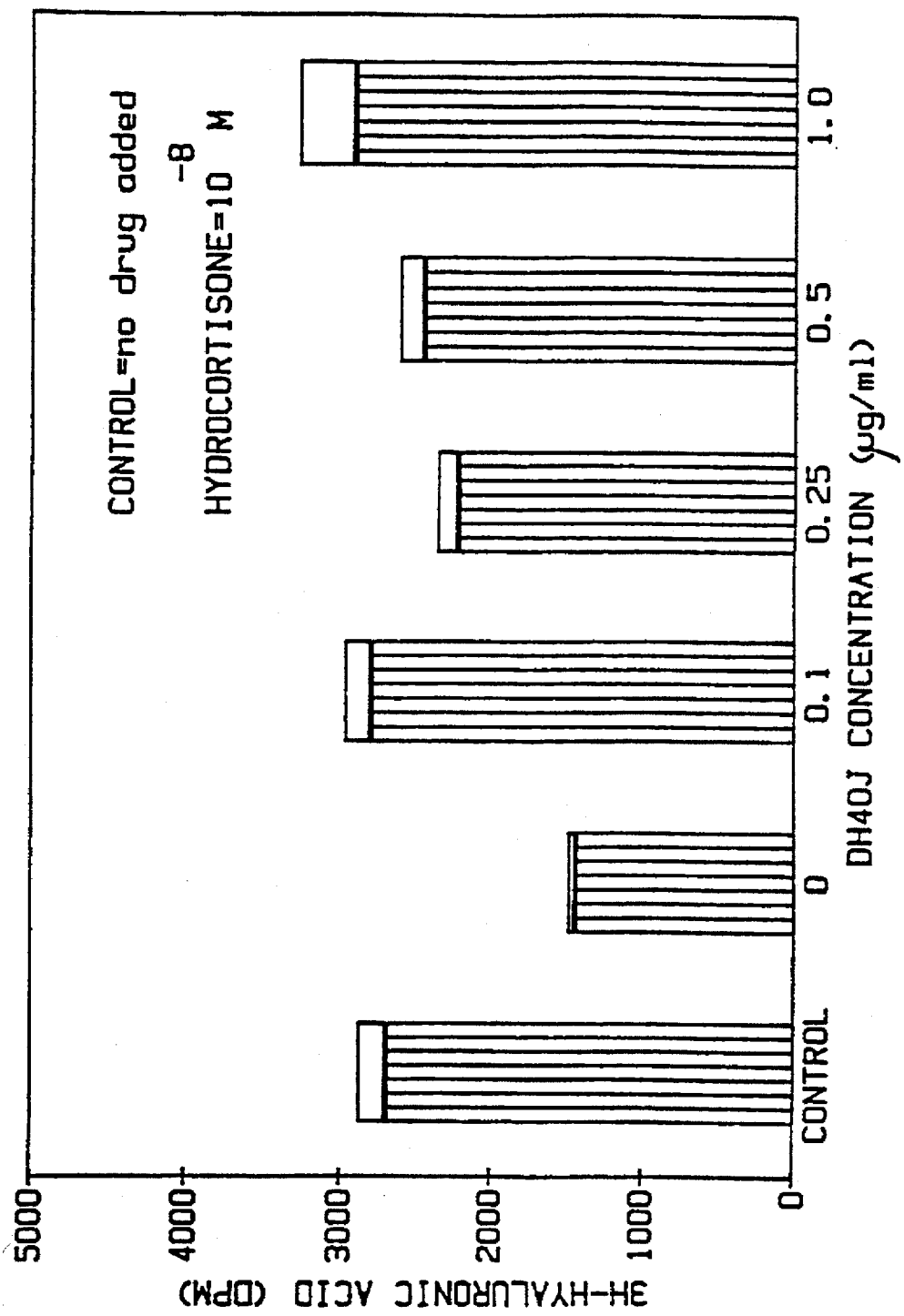

FIG. 22—Combined effects of hydrocortisone (at $10^8$M) and DH40J at various concentrations on the in vitro biosynthesis of hyaluronic acid (HA) by synovial fibroblasts derived from OA joints.

Polysulphated polysaccharides such as heparin and those derived from chondroitin, keratan, dermatan, chitin, dextran (polyglucoses), xylans (polypentoses), starch, amylopectin, cellulose, amylose, alginic acid, pectin, inulin and hyaluronic acid have been shown to have a variety of biological activities. Note that heparin is the only naturally occurring polysulphated polysaccharide. The most widely studied activities includes inhibition of acid and neutral proteinases (e.g. human granulocyte elastase, HGE) and lysosomal hydrolases (e.g. hyaluronidase), anti-viral (e.g. Herpes Simplex), anti-inflammatory and anti-coagulant activity.

In some instances the potency of the biological activity of a particular polysulphated polysaccharide has led to its commercial development. One example is Arteparon® (trade mark of Luitpold-Werk) which consists predominantly of polysulphated chondroitin. This compound has been used as an anti-arthritic drug.

Another example is SP54® (trade mark of Benechemie GmbH) which is a pentosan polysulphate sodium salt. This compound has found wide application as an anti-thrombotic, anti-arteriosclerotic, and anti-hyperlipidaemia agent.

SP 54® (trade mark of Benechemie GmbH) is the sodium salt of a semi-synthetic polysulfated xyloside having an average molecular weight of about 6000 Daltons and a sulphur content of about 16%. This compound has been known since the early 1960s to be a synthetic heparinoid and an anti-thrombotic agent. The structural formula is shown below.

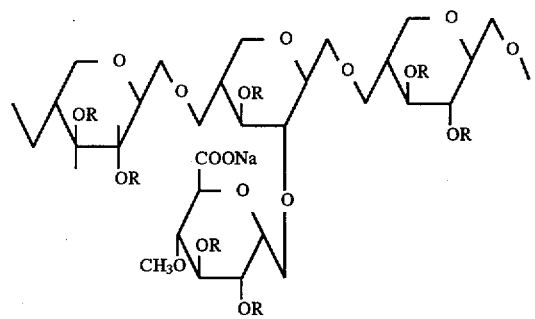

in which R represents the group —SO₃Na or hydrogen

Its properties were described in a paper by Halse, Th, entitled: "Aktivierung Der Fibrinolyse Und Thrombolyse Durch Polysaccharidschwefel-Saureester" Arzneim. - Forsch 12, 574 (1962). This compound has also been found to have some anti-inflammatory properties as reported by Kalbhen, DA, in Pharmacology 9, 74 (1973).

That SP 54 will inhibit PMN elastase and other enzymes has been known for some time and it is known that PMN elastase is a potent degrader of connective tissues, including articular cartilage. Consequently, investigators have attempted to elucidate the mechanism of inhibition with a view to discover the possible role of anti-inflammatory and anti-rheumatic drugs as proteinase directed inhibitors. An example of one such investigation is that reported by Baici et al in Biochem. Pharmacol. 30, 703 (1981). In this latter paper, SP 54® was shown to be a potent inhibitor of proteolytic and hydrolytic enzymes.

In addition, Andrews et al in Chem. Biol. Interactions 47, 157 (1983) have shown that SP 54® binds to articular cartilage and connective tissues.

Without being bound by theory, the present inventors believe that SP 54® may function by protecting articular cartilage and other connective tissue from breakdown in the pathological state as well as stimulating their repair and restoration of normal function.

Arteparon® is a mucopolysaccharide polysulphuric acid ester produced by Luitpold GmbH. More specifically, it is a heterogeneous semi-synthetic glycosaminoglycan polysulfate in which the predominant (about93%) disaccharide repeating unit is hexuronic acid glycosidically linked to galactosamine. Approximately four of the free hydroxyl groups of the disaccharide repeating unit of Arteparon are esterified by sulfate groups to give a sulfur content of about 13.0% by weight. The commercial preparation has a molecular weight of about 10,000 Daltons.

Figure 1:
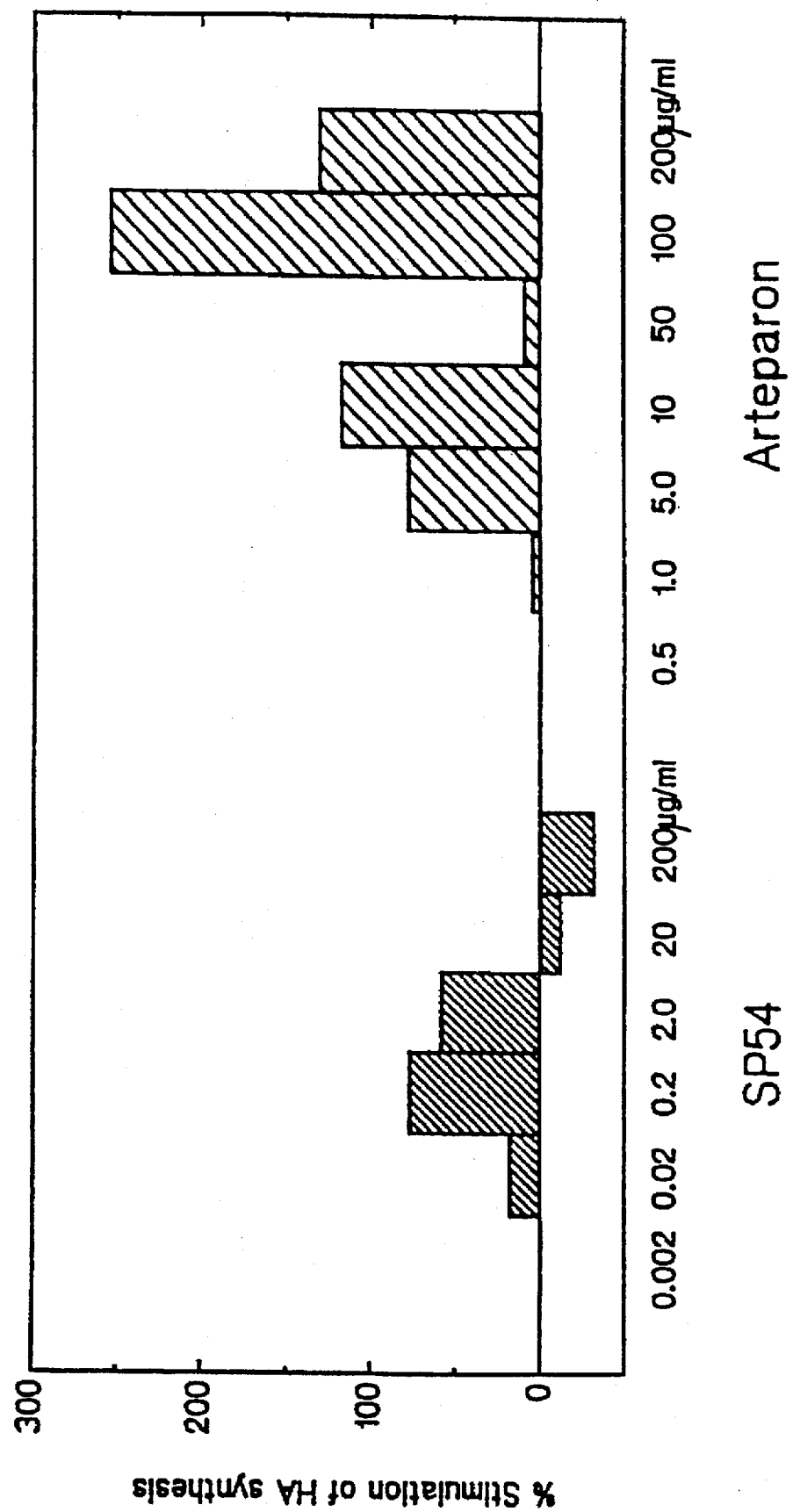
FIG. 1—Effects of Pentosan polysulphate (SP54®) and Arteparon® at various concentrations on the in vitro biosynthesis of hyaluronic acid by human synovial fibroblasts.
Figure 2:
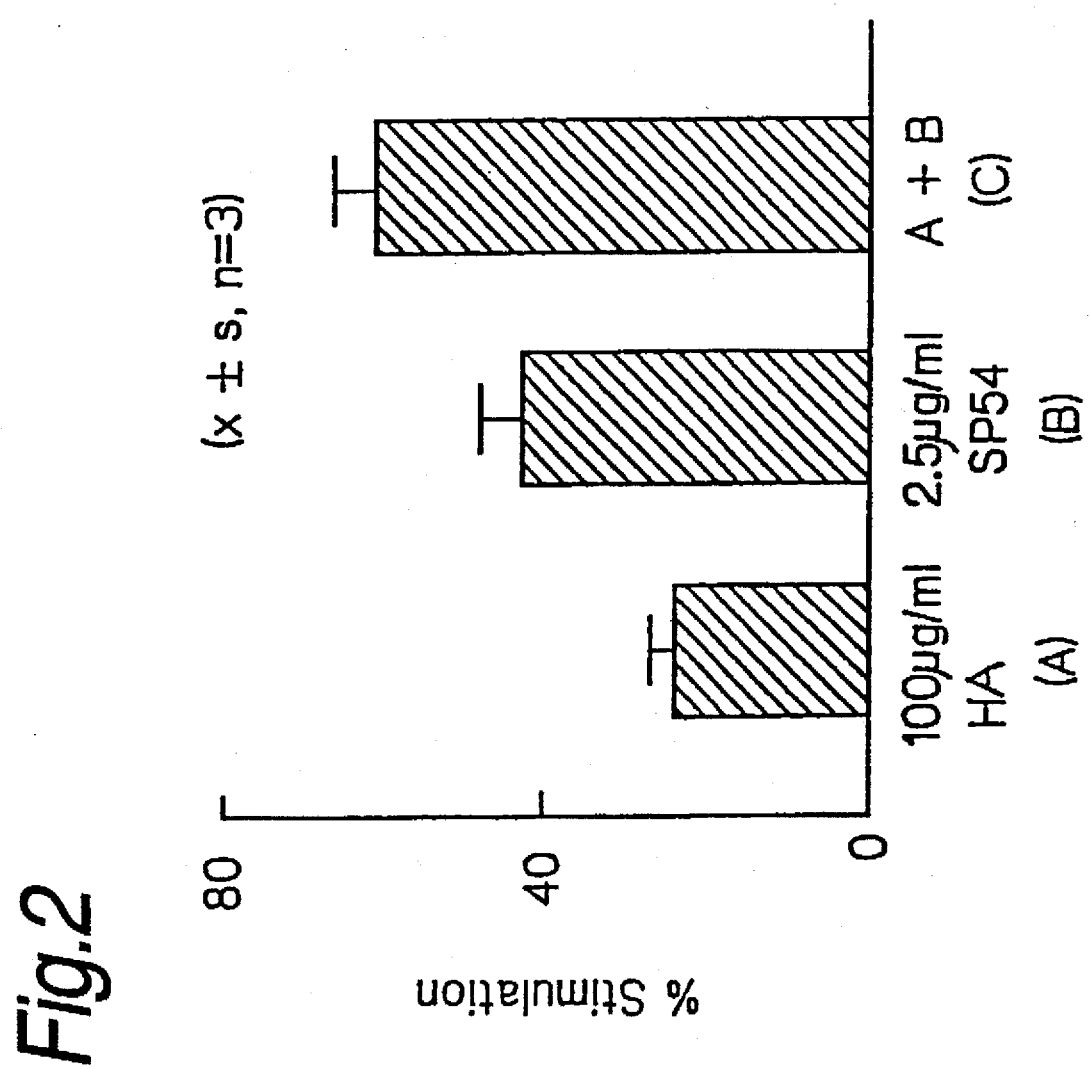
FIG. 2—Effects of (A) hyaluronic acid (HA) alone, (B) Pentosan polysulphate (SP54®) alone, and (C) a combination of HA and SP54 on the in vitro biosynthesis of HA by human synovial fibroblasts.

Illustrative of this effect is the data shown in FIG. 1 where in can be seen that SP54 and Arteparon® stimulates the biosynthesis of hyaluronic acid (HA) in human OA synovial fibroblasts in a concentration manner. It should be noted that while the stimulatory effect of Arteparon on HA biosynthesis is known (Verbruggen and Veys), Acta. Rhumatol Belg. 1, 75–92, 1977) that of SP54 has not been previously reported). A recent publication by Smith and Ghosh in Rheumatology International 7, 113–122, 1987 demonstrated that high molecular weight (>3.0×$10^6$ Daltons) HA could also stimulate de novo HA synthesis by synovial fibroblasts and the present inventors have found that this effect is augmented by the addition of Arteparon® or SP54® to the high molecular weight HA preparation. This is illustrated in FIG. 2 where it can be seen that the addition of a combination of high molecular weight HA and SP54 to synovial cells in culture leads to a greater synthesis of HA than if either agent was used alone.

The substances, SP54® and Arteparon® are potent inhibitors of proteases, which destroy joint articular cartilage. They also suppress the egress into the joint of inflammatory cells, such as PMN cells which as previously mentioned are responsible for hyaluronate breakdown. In this way, the inventors believe that SP54 and Arteparon both protects and promotes normalization of joint hyaluronate and articular cartilage and work in combination with high molecular weight hyaluronate which provides the rheological properties necessary for efficient biomechanical function.

Although the aforementioned polysulphated polysaccharides of the first and second aspects of the invention have found a diversity of clinical applications, their basic structural similarity as linear polyanions has resulted in a profile of biological activities which are shared by most members of this chemical family. Naturally, however, the biological activities of each of the members varies, not necessarily in any predictable manner.

Further, it must be appreciated that whilst such a spectrum of biological activities may be of considerable scientific interest in cases where the biological activities of a compound conflict, such compound could be deleterious as an agent to be used for therapeutic purposes.

One example is that in the treatment of arthritis, the patient is generally administered daily doses of a suitable drug for several months or years and should the drug used also suppress blood clotting mechanisms i.e. have anti-thrombotic, fibrinolytic, or thrombocytopenic activity, haemorrhage following acute injury or menache may occur.

In relation to the polysulphated polysaccharides, a number of compounds have been shown to have potent anti-thrombotic or anti-coagulant activity, which has therefore limited the use of such compounds particularly in long term therapy of the type outlined above.

Some selectivity of biological action of the polysulphated polysaccharides is therefore desirable and has been achieved by varying the degree and position of sulphate substitution in the polysaccharide rings.

The molecular weight of polysulphated polysaccharides has also been shown to be a determinant of biological activity. Thus, it has been report by Ricketts in Biochem. J. 51, 129–133 (1952) that for the dextran polysulphates, the high molecular weight analogues were more toxic than the low molecular weight species. It was also found that the degree of sulphation was an important determinant of anti-coagulant activity. In addition the anti-coagulant properties of the heparins have also been shown to be dependent on the molecular size of fractions used. (Casu, B, in Advances in Carbohydrate Chemistry and Biochemistry 43, 51–134, 1985).

In a more recent paper, published in Archives Internationales de Pharmacodyanamie de Therapie, 282 (2) 196–208 (1986), the authors showed that a high molecular weight analogue of SP54® (SR 24751) and SP54® where active in vitro in improving proteoglycan incorporation into the extracellular matrix. However, a low molecular weight fraction of SP54® (SR 25491) and Arteparon® (Registered trade mark of Luitpold-Werk GmbH) were inactive.

It is preferred that the hyaluronate used in the said combinations is of a molecular size lying within the normal size range found in the joint of the animal to be treated. In the case where humans are treated, a preferred source of the hyaluronate is that obtained from bovine synovial fluid by a method disclosed in the PCT application of D. Cullis-Hill, PCT/AU86/00129.

As already mentioned, corticosteroids are extremely potent anti-inflammatory agents with widespread application in both veterinary and human medicine. The limitation of this useful property is the suppressive effects of these drugs on connective tissue metabolism which in itself can be extremely harmful to the joints and tissues so treated. In this regard the present inventors have found that by using combinations of anti-inflammatory corticosteroids and sulphated polysaccharides such as xylan polysulphate, Arteparon®, dextran sulphates, dermatan polysulphate, chitosan polysulphate, and the like that the degenerative effects of the corticosteroid may be attenuated.

For example it is known that the weekly intraarticular administration of hydrocortisone for eight weeks will induce the loss of proteoglycans (PGs) from joints of rabbits so treated (Oegema and Behrens, Archives of Biochemistry and Biophysics, 2206, 277–284, 1981). The present inventors have found, however, that when this glucocorticoid is administered in combination with the inventive polysulphated polysaccharides, degradation and loss of proteoglycans from joint cartilages can be prevented.

The results obtained for hydrocortisone (50 mg) and pentosan polysulphate (5 mg) when administered intra-articularly to rabbits, relative to hydrocortisone (50 mg) alone are shown in Table 1. As can be seen the hydrocortisone-SP54® combination reduced loss of hexuronate (a measure of proteoglycan content), restored PG extractability and elevated the de novo biosynthesis of matrix $^{35}$S-labelled PGs (specific activity).

Those inflammatory joint diseases which may be effectively treated with the present invention include arthritis, tendoniris and bursiris. By effective treatment, it is meant that pain associated with the disease is reduced and normal joint function is restored.

The preferred method of administration of the composition of the invention is by direct injection into the appropriate pathological tissues, for example, the synovial cavity of an arthritic joint. In such cases, the carrier would be normal sterile physiological saline. However the inventors have also found that the inventive compositions when used in higher concentrations may be employed systemically (intra-muscularly, sub-cutaneously, intravenously topically).

The actual amount of hyaluronate or corticosteroid and compound capable of maintaining the integrity of connective tissues administered, may vary widely depending on the size of the species of animal to be treated, the pathology of the tissue or joint and the tissue or joint to be treated.

In one example of the invention, it was found that in the canine, an injection containing 5 mg of sodium hyaluronate and 5 mg of SP 54 dissolved in 1 ml of sterile saline injected into the stiffle joints or the metacarpal joints of animals troubled with traumatically induced or

TABLE 1

ANALYSIS OF MATURE RABBIT ARTICULAR CARTILAGE AFTER 8 WEEK TREATMENT WITH INTRA-ARTICULAR CORTISONE OR CORTISONE - SP54 COMBINATION, RELATIVE TO NON-DRUG TREATED ANIMALS

| Parameter | Group 1 (G1) Non-drug Treated Controls (n = 4) | Group 11 (G2) Cortisone Treated Joints (n = 4) | Group 3 (G3) Cortisone + SP54 Treated Joints (n = 4) | Statistical Analysis* |
|---|---|---|---|---|
| Hexuronic Acid(UA) | 27.5 | 27.4 | 29.7 | G1 > G2(p < 0.03) |
| (ug/mg dry wt.) | 36.1 | 23.2 | 29.7 | G1 = G3 |
|  | 28.9 | 20.0 | 22.3 | G2 < G3(p < 0.02) |
|  | 36.4 | 21.8 | 24.6 |  |
| Mean ± SD | 32.3 ± 4.7 | 23.1 ± 3.1 | 26.7 ± 3.7 |  |
| 4M Gu HCl,PG | 60.4 | 53.2 | 62.3 | G1 > G2(p < 0.05) |
| Extractability (%) | 56.3 | 57.6 | 57.8 | G1 = G3 |
|  | 56.5 | 56.8 | 64.5 | G2 < G3(p < 0.03) |
|  | 74.2 | 51.5 | 57.8 |  |
| Mean ± SD | 61.9 ± 8.4 | 54.7 ± 2.9 | 60.6 ± 3.3 |  |
| $^{35}$S-PG Specific | 826.7 | 896.8 | 891.5 | G1 = G2 |
| (DPM/ug UA) | 1124.1 | 866.6 | 1072.8 | G1 = G3 |
|  | 748.7 | 1061.4 | 1236.5 | G3 > G2 |
|  | 614.4 | 854.2 | 931.4 | (p < 0.05) |
| Mean ± SD | 828.5 ± 215.7 | 919.7 ± 96.1 | 1033.1 ± 156.4 |  |

*Analysis of Variance Using Student-t-Test.
p < 0.05 = Statistically significant inflammatory arthritis, resulted in the recovery of function within five days of administration.

In the case of the horse, however, 25 mg of hyaluronate in 2 ml of sterile saline could be used in combination with 25, 50 or 100 mg of SP 54 depending on the joint or tissue to be injected.

For corticosteroid/pentosan polysulphate combinations, excellent clinical results have been obtained in lame racing greyhounds with 5.0 mg of the pentosan polysulphate and 20 mg of the corticosteroid administered once only as a single injection into the affected joint. When administered intramuscularly 50 mg of pentosan polysulphate was used with 80 mg of hydrocortisone or methyl prednisolone acetate.

Naturally, it would be expected that alkali metal sales other than the sodium salt (SPS®), would have a similar effect.

Although the present inventors have found that the polysulphated polysaccharides of the first aspect of the invention are useful in compositions including either corticosteroids or hyaluronic acid, or water soluble sales thereof, the present inventors have further found that when the polysulphated polysaccharides are present as particular complexes,the suppression of blood clotting mechanisms by the polysulphated polysaccharides is greatly reduced whilst the anti-arthritic, anti-inflammatory activity is enhanced. The effective polysulphated polysaccharides are believed to be those polysaccharides selected from the group consisting of dextran, xylan, chondroitin, dermatan and hyaluronic acid. The effective complexes are those formed between the aforementioned polysulphated polysaccharides and multivalent metal ions, $Ag^+$ and $Au^+$, and quaternary ammonium compound complexes.

The preferred polysaccharide is xylan polysulphate, most preferably SP54®.

The particular complexes are selected from the group consisting of $Ag^+$, $Au^+$, $Ca^{2+}$, $Mg^{2+}$, $Ba^{2+}$, $Pb^{2+}$, $Cu^{2+}$, $Zn^{2+}$, $Au^{2+}$, $Pd^{2+}$, $Pd^{4+}$, $Pt^{4+}$, $Pt^{2+}$, trivalent metal ions, and quaternary ammonium compound complexes. Examples of the latter compounds are pyridinium chloride, tetraalkyl ammonium chloride, choline chloride, cetylpyridinium chloride, N-cetyl-N,N,N-trialkylammonium chloride or their derivatives.

The most preferred of these is the zinc complex.

The inventors are aware of Australian patent application 24412/84 (Sanofi et al) in which there is disclosed particular xylan sulphates which are claimed to have broadly enhanced anti-thrombotic and anti-coagulent activity compared with heparin. The essence of this invention is the selection of particular molecular weight fractions and degrees of sulphation of SP54. Further, it is noted that the inventors state that compositions of the invention may be useful in treating rheumatoid arthritis, arthrosis and osteoarthritis. However, such properties are not quantified in any way and as SP54 is known to have such activity, the suggestion that the compositions of the invention may be useful in such therapy is hardly surprising.

The inventors are also aware of US4465666 (Lukas et al) and EP12115 (Lukas et al) in which there are disclosed compositions containing zinc ions and an acid sulphated polysaccharide or polymer chosen from heparin dextran sulphate and polyvinyl sulphate. It is also disclosed that other acid sulphated polysaccharides may be used such as chondroitin sulphate, carragheenan, sulphated polypentosan, sulphated dextrans and sulphated polyglucoses. In addition, pharmaceutically acceptable salts such as the potassium and sodium salt of these acid sulphated polysaccharides are also taught as being effective.

However, this prior art does not disclose the compounds of the present invention nor suggest that such compounds would have the utility found by the present inventors.

The present inventors have shown that because of the unusually strong affinity of the metal in these complexes of the invention for certain sulphate esters and oxygen atoms present on the carbohydrate rings of the polysaccharide, the metal alters the conformation and rigidity of the polymer chain thereby influencing its biological activity.

This biological activity occurs only when the complexes are prepared according to the methods described herein, or their equivalents, since they are well defined compounds as shown by microanalysis and $^{13}$C-NMR spectroscopy. Moreover, by simply mixing zinc ions and sulphated polysaccharide in a variety of ratios (as described by US4465666 and EP 12115 (Lukas et al) as a means of confering antiviral activity) did not reproduce the biological activity of the metallo complexes described in this invention as demonstrated by three examples described in the section following on biological activities.

Some explanation of the antiviral activity of the mixtures prepared by Lukas et al might be attributed to the high molecular weight polymers they utilize e.g. Dextran sulphates M.W. $8 \times 10^4 – 2 \times 10^6$ were given as examples whereas in the present invention polymers with MWs of 30,000 or less were utilized. (e.g. Dextran sulphates, 5–10,000 Da and Xylan polysylphates 3–10,000). It should also be noted that the very high ratio of polysulphated polysaccharides to zinc were used by Lukas et al which for the most part are far in excess of that existing in the pure compounds claimed.

The present inventors believe that the $Ag^+$, $Au^+$, divalent metals including $Ca^{2+}$, $Mg^{2+}$, $Ba^{2+}$, $Pb^{2+}$, $Cu^{2+}$, $Zn^{2+}$, $Au^{2+}$, $Pd^{2+}$, $Pt^{2+o}$, trivalent metal ,, $Pd^{4+}$, $Pt^{4+}$ complexes and the quaternary ammonium complexes are novel and non-obvious compounds. Furthermore, it has been found that the zinc complex is effective alone in the treatment of arthritis and related inflammatory joint diseases. The inventors believe that the other complexes would have a similar property.

The inventors have also found that the unique biological activity of the sulphated polysaccharides induced by chelation with divalent and trivalent metals is not confined to 100% substitution of available sites by these substituents. Thus on a weight/molar basis they have found that multivalent, particularly, divalent or trivalent metal substitution of monovalent ions between the range of 1%–100% may also induce conformational changes in the polysulphated polysaccharide-thereby influencing its biological activity. Examples for 8.5%, 83% and 100% substitution of sodium ions by zinc ions in the sulphated xylans are given as typical examples of this effect.

The $^{13}$C-NMR data derived from the three zinc-pentosan polysulphate penetration complexes 8.5% Zn (DH40G), 83% Zn (DH40J) and 100% Zn (DH40Y) showed that as the amount of zinc chelated increased the binding increased. From this we may deduce that the rigidity of the conformation of the complexes increased in the order DH40G (8.5% zinc) DH405J (83% zinc) DH40Y (100% zinc) and from the biological data it would appear that total substitution of all $Na^+$ by zinc may lead to a conformation which is very rigid.

As a consequence of this, the formation of these metallo-polysulphated polysaccharide complexes provides a useful means of transporting selected metals into bodily tissues, since unlike the known salts of the polysulphated polysaccharides like sodium, potassium, or ammonium, which dissociate into the respective ions when dissolved in water, the complexes of the present invention do not dissociate in a aqueous or physiological media.

Figure 3A:
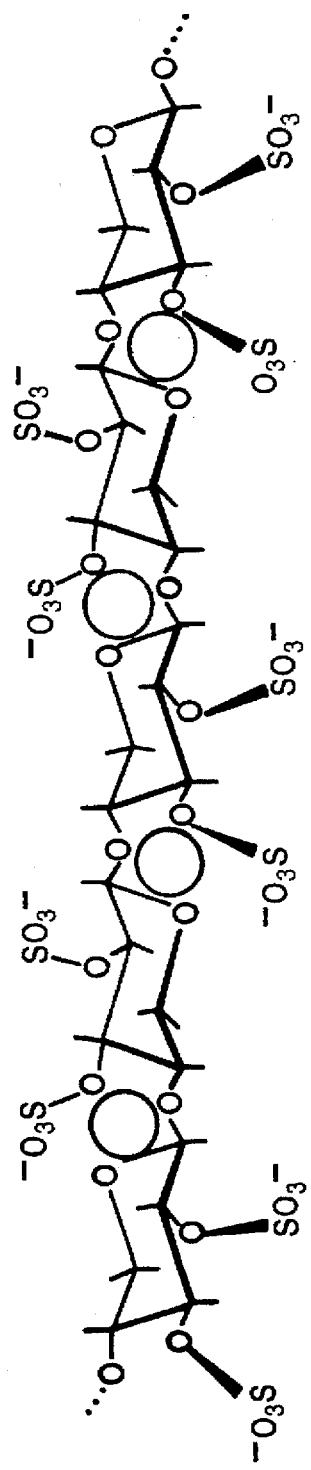
FIG. 3—From the $^{13}$C-NMR data the position of the zinc [A] and calcium [B] atoms in the complexes formed with Pentosan polysulphate are shown as black spheres. Note that in the zinc complex [A] the metal resides in the cleft between the pentosan rings, whereas in [B] the calcium occupies a position across the C-3 and C-5 positions of the sugar ring and close to the sulphate groups.

Zinc and to lesser extent $Mg^{++}$ by virtue of their ionic radii and electronic configuration appear from the $^{13}$C-NMR spectroscopic studies described herein to occupy sites within the polysulphated polysaccharide chain which are quite different to the larger atoms —$Ca^{++}$, $Cu^{++}$, $Ba^{++}$, $Fe^{++}$etc. The conformations adopted by these respective complexes is shown in FIG. 3(A) and (B) where it is evident that in the case of pentosan polysulphate complex, zinc occupies a position in which the oxygen of the glycoside linkage and oxygens to the sulphur esters in the 2 and 3' positions in adjacent rings can efficiently interact with it. It is these multiple site interactions and ability of zinc to fit into the space available between rings which render these complexes energetically favourable and thus stable. Significantly the biological activity of the zinc complexes are different to the metal complexes formed with other metals. (See section on biological activity).

The compounds of the invention have particular utility in the treatment of rheumatoid arthritis, osteoarthritis and related inflammatory joint conditions as well as cancer and wound healing. These compounds are also anti-viral.

Inventors believe that this utility stems from the ability of the compounds of the invention to inhibit the release and the action of the serine proteinases, e.g. human granulocyte elastase (HGE), plasminogen activator and rumour derived elastase, The importance of this inhibition is that in osteo- and rheumatoid arthritis, the proteoglycans of joint articular cartilages are depleted due to excessive degradation by proteinases. Note that proteoglycans of the extracellular matrix confer the property of resilience and are therefore essential to the biomechanical performance of these tissues.

In all tissues, rumour cell metastasis is dependent on the breakdown of the extracellular matrix to allow proliferation and migration of the neoplastic cells to other sites. A proliferating rumour mass also requires a good blood supply for survival and breakdown of the matrix to allow penetration of blood vessels is also a prerequisite for rumour expansion within the host tissue. Tumour cells and activated endothelial cells of the blood capillaries achieve this objective by the release of enzymes which can directly and indirectly degrade the extracellular matrix. Of particular importance are the serine proteinases (such as the plasminogen activators and elastase like enzymes) used by the rumour cells to activate blood borne zymogens e.g. plasminogen, and normal connective tissue cell latent enzymes, e.g. metallo proteinases (collagenase, proteoglycanases etc), and serine proteinases zymogens which can directly and indirectly degrade the components of the extracellular matrix. The inventive metallo polysulphated polysaccharides are potent inhibitors of the serine proteinases produced by mammalian rumour cells lines and thus have potential utility as anti-cancer/anti-metastatic agents. The particular metal ions likely to be effective are $Ag^+$, $Au^+$, $Au^{2+}$, $Pd^{2+}$, $Pd^{4+}$, $Pt^{2+}$ and $Pt^{4+}$.

At the same time, inventors have demonstrated that the compounds of the invention are less effective anti-coagulants than when in an uncomplexed form. Therefore, given the long term therapy associated with treatment of such inflammatory joint diseases, this reduction in anti-coagulant activity is of significant benefit.

Moreover, it has been found that the compounds of the invention are capable of stimulating mitosis and DNA synthesis in a variety of connective tissue cell lines. (e.g. fibroblasts, chondrocytes, fibrochondrocytes) and together with their ability to promote matrix component (proteoglycan, hyaluronate and collagen) biosynthesis are of immense benefit in the healing and repair of damaged tissues. Examples of these useful biological properties are provided.

Preparation Polysulphate Polysaccharide—Metal Complexes

These are prepared from the polysulphated polysaccharides which may be obtained from commercial sources e.g. dextran sulphates MW 5000 or 8000, Sigma Chemical Co., St. Louis, Mo., U.S.A., pentosan polysulphate (SP54®) Benechemie, Arzneimittell, Munchen, F.R.G.

Chondroitin polysulphate (Arteparon®, Luitpold Werk, Munchen, F.R.G. or by sulphation of commercially available polysaccharides e.g. xylans (Sigma Chemical Co. St. Louis, Mo. U.S.A., Fluka Chemical Co., Switzerland; dextrans, chitin, and amylose from Biocarb Chemicals, Lund, Sweden, or sulphation of polysaccharides isolated from natural source as described by Wilkie, Advances Carbohydrates, Chem. and Biochem. 36, 215–264 (1970), or Whistler and Richards in "Hemi cellulose" in Carbohydrate 2nd Ed. Vol II A (1970) Ed. Pigman & Horton, Academic Press or other reviews describing their extraction and purification.

(A) Sulphation of Polysaccharides

Example—Preparation of Xylan Polysulphate

Dry, commercially available xylan (from larchwood, or oat spelts, Sigma Chemical Co., St. Louis, Mo., U.S.A.), or as isolated from other sources as described by Whistler and Richards in the "Hemicellulose in the Carbohydrates" 2nd Ed. Vol. IIA (1970) Eds. Pigman & Horton, Academic Press, is sulphated by adding with rapid stirring to cooled chlorosulphonic acid in dry pyridine using the general method of Ricketts in Biochem. J. 51, 129–133 (1952). The xylan-chlorosulphonic-pyridine mixture was maintained at 65° for 6 hours, cooled and poured with vigorous shaking into crushed ice. A strong (40% w/v) NaOH solution was then added until the solution reached pH7. The solution was filtered and ethanol added to precipitate the crude polysulphated xylan as a syrup. The syrup was separated, redissolved in water and subjected to a series of ethanol/water precipitations to afford a final syrup which was dissolved in water (pH=2.0) and dialysed against water. The non-dialysable salt free polysulphated xylan was then obtained as the sodium salt by lyophilization. This sulphation method is essentially that described by Ricketts (ibid) for the preparation of the sodium salts of the dextran polysulphates. Fractionation of the sulphated xylan into the desired molecular sizes was then achieved by dissolving the sodium salt in a buffer of high ionic strength of 0.5M NaCl and subjecting the solution to gel filtration chromatography using Sephadex G75 or Sephacryl G200 columns. Alternative methods of fractionation include high performance liquid chromatrography, membrane filtration, or hollow fibre techniques e.g. using Amicon RA 2000 system with 10,000 MW cut off filter or ion exchange chromatography using the method described by Doctor and Sauls in Thrombosis Research 30, 573–578 (1983).

(B) Conversion of the Sulphated Polysaccharide to Metalle chelate complexes

Example Preparation of DM40Y (100% Zinc substitution), DH40J (83% substitution) and DH40G (8.5% substitution)

Method 1: The sodium salt of Xylan polysulphate (as prepared above, or as purchased commercially as SP54®) (50.0 gram) was dissolved in 100 ml distilled water and passed down a cation exchange column, such as Dowex 50W-X2 (20–50 mesh) which had been previously converted to its acidic form ($H^+$). Sufficient resin was used to ensure complete exchange of the sodium ions of the xylan polysulphate by $H^+$. For 50.0 grams of SP54® 500 grams of resin was sufficient. Fractions were monitored for pH using a pH electrode and sulphated polysaccharide using the method of Farndale, Sayers and Barrett in Connective Tissue Research 9, 247–248 (1982). The free acid eluted from the column in the first 200 ml, these fractions were pooled and an aliquot converted directly into the zinc complex by neutralation with an equivalent molar amount of a zinc salt. By using a basic zinc salt (e.g. Zn Acetate) the end point of this neutralisation can also be determined potentiometrically.

The mixed sodium-zinc-Xylan polysulphate complexes (DH40G and DH40J) were obtained by adding to the Xylan polysulphate free acid solution the appropriate amount of a solution containing the $Zn^{++}$ and $Na^+$ ions in the required proportions. Again the acetate salts of these metals was used since the change of pH for neutralisation was easy to monitor. Any combination of salts in any proportions can be produced by this method but in some cases the salts of the polysulphate polysaccharides precipitate. This occurred for the $Ba^{++}$ and $Pb^{++}$ complexes of Xylan polysulphate and dextran polysulphates. In contrast the $Zn^{++}$ complexes were highly water soluble.

Method 2: The free acid form of the xylan polysulphate prepared as described in Method 1 was passed down a cation exchange column (e.g. Dowex 50W-X2, or Duolite C25), which had been converted to the cationic form required for exchange (e.g. $Zn^{++}$, $Mg^{++}$, $Cu^{++}$, $Ca^{++}$ etc.). The metal sulphated xylan complex was eluted from the column with distilled water and fractions monitored using the Farndale, Sayers and Barrett method described in Method 1.

Method 3: A cation exchange resin generated as the $H^+$ form was converted into the metal ion form by equilibrating with at least two bed volumes of the salt of the metal (e.g. Zn $SO_4$, $CuSO_4$, $MgSO_4$, $CaSO_4$). Complete conversion was achieved when no more $H^+$ was eluted from the column. Unexchanged metal ions were then completely washed from the column. It is essential to be certain at this step that no free $H^+$ form remains in the resin. The sodium salt of the sulphated polysaccharide was then passed down the column eluting fractions with distilled water, whilst monitoring for sulphated polysaccharides (Farndale et al ibid) and the metal using appropriate assays (e.g. $Cu^{++}$ spectroscopically, $Zn^{++}$ by atomic absorption spectroscopy). The metallopolysulphated polysaccharide complexes can then be isolated from the collected pooled fractions by lyophilization or ethanol precipitation. However, with the latter method the required complex often precipitates as an oil and requires agitation and cooling for crystallisation to be induced.

Confirmation of Complexation Formation (a) Atomic Absorption Spectroscopy

Previous analysis of the sodium salts of pentosan polysulphates (e.g. SP54®) had demonstrated that even under exhaustive conditions the maximum sulphate substitution obtained was on average 1.8 esters per repeating unit. The reasons for this are unclear but since these molecules are polydispersed systems derived from natural sources the number of hydroxy groups available for substitution may be variable. However for he purposes of analysis it is customary to make allowance for this in the empirical formulae. Thus the empirical formula of DH40Y, which was the fully substituted zinc pentosan polysulphate derivative would be

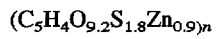

where n=17 to give the experimentally determined molecular weight mean average (($M_w$) of 5,564.

As can be seen from Table 2, the experimental derived Zn value of 17.9% is in reasonable agreement with the calculated value of 17.2% bearing in mind that the empirical formula for these naturally derived polymers is less precise than for totally synthetic molecules. The mixed salt ($Zn^{++}$/$Na^+$) systems DH40J and DH40G were analysed for Zn content and from these values the empirical formula was calculated (see Table 2).

(b) Gel Filtration Chromatography

An acid washed (to remove bound zinc) precalibrated column (20 cm×0.6 cm) of Sephadex G25 was equilibrated for 24 hours with 50 mM Hepes/NaOH buffer pH 7.0. One ml of a solution of DH40G made up in the elution buffer (1.0 mg/ml) was applied to the column at a flow rate of 10 ml/hour. Fractions collected were monitored for sulphated xylan using the Farndale assay as described in Connective Tissue Res. 9, 247–248 (1982) and for zinc using atomic absorption spectroscopy. As is evident from FIG. 4, the majority of zinc eluted in the void volume fractions ($V_o$) of the gel filtration column also corresponds to the maximum sulphated xylan absorption measured by the Farndale assay. Under the elution conditions used, unassociated zinc ions would have eluted at $V_t$ of the column.

(c) NMR Studies

$^{13}$C-NMR proton decoupled spectra (50.1 MHz) of SP54 and metallo complexes in $D_2O$ were obtained on a Jeol FX-200 FT spectrometer. Samples were dissolved as 10 (w/v), aqueous solutions. Only Milli-Q deionised water was used to avoid foreign cation contamination of samples.

TABLE 2

Zn analysis derived from atomic absorption spectroscopy

| Compound | Subunit Empirical Formula | Subunit MWt. | CALC $Zn^{++}$ | Found $Zn^{++}$ | % $Zn^{++}$ Substitution | % $Na^+$ Subtitution |
|---|---|---|---|---|---|---|
| DH40Y | $C_5H_4O_{9.2}S_{1.8}Zn_{0.9}$ | 327.3 | 17.2 | 17.9% | 100% | 0% |
| DH40J | $C_5H_4O_{9.2}S_{1.8}Zn_{0.75}Na_{0.3}$ | 324.5 | See Below* | 15.0% | 83% | 17% |
| DH40G | $C_5H_4O_{9.2}S_{1.8}Zn_{0.08}Na_{1.6}$ | 310.8 | See Below* | 1.6% | 8.5% | 91.5% |

*The Zn/Na molecular ratios were determined from the experimentally derived values.

Solutions PD=7.0 which contained an internal standard (in a co-axial tube) of acetonitrile. The sample temperature was 37°, spectral width 10 KHz and 16K data points were used. Chemical shifts of ring carbon atoms were determined relative to the internal standard and were presented as parts per million (ppm). Differences between chemical shift values were express in Δ Herz units (α Hz).

As is evident from Table 3 the $^{13}C$-chemical shifts for the penrose ring carbons of SP54®, the sodium salt of xylan polysulphate are different to those obtained for the divalent metal complexes. These differences were more readily appreciated by using the α Hz values, which were derived as the difference between the chemical shift of a particular carbon in SP54® and the same carbon of the metallo complex (Table 4). For the fully substituted zinc complex DH40Y it can be seen that the greatest increase in shift difference (α Hz) occurs for carbons 4, 2 and 5 where electron deshielding occurs. In contrast carbons 1 and 3 are shielded (-ve shift) relative the same atoms of SP54®. These data indicate that the zinc atom in DH40Y must reside in a position which is close (<4 Å) to carbon atoms 4, 2 and to lesser extent 5, but further away from carbons 1 and 3. The magnitude of these shifts was dependent on the degree of zinc substitution in the complex, for as shown in Table 4, the 83% (DH40a) and 8.5% (DH40G) had lower α Hz. From these results we may conclude that as more sites in the pentosan polysulphate molecules are occupied by zinc atoms, the conformation changes to make the binding tighter.

While the magnesium complex of pentosan polysulphate showed similar chemical shift trends to the zinc derivatives, the changes were less marked indicating that the "molecular fit" and atomic interactions were less effective than in the $Zn^{++}$ complex.

Using the information shown in Table 4 and molecule models of part of the pentosan polysulphate chain, it is possible to predict the site most likely occupied by the zinc and magnesium atoms. This is shown diagrammatically

TABLE 3

$^{13}C$—NMR chemical shift values (PPM) for sodium pentosan polysulphate (SP54$^R$) and some divalent metal complexes

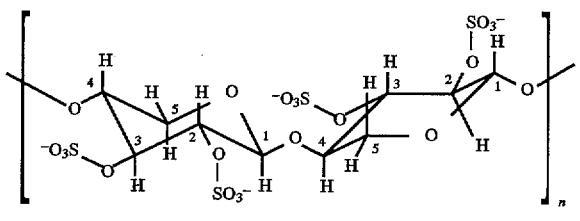

| Compounds | Ring Carbon Shift (PPM) | | | | |
|---|---|---|---|---|---|
| | 1 | 2 | 3 | 4 | 5 |
| SP54$^R$ (100% Na) | 99.6455 | 73.4232 | 74.5422 | 72.9854 | 59.3635 |
| DH40Y (100% Zn) | 99.4752 | 73.8368 | 74.289 | 73.5449 | 69.4608 |
| DH40J (83% Zn) | 99.4995 | 73.7395 | 74.3719 | 73.3503 | 59.4364 |
| DH40G (8.5% Zn) | 99.6455 | 73.5692 | 74.5422 | 73.1857 | 59.4364 |
| DH70 (100% Mg) | 99.4752 | 73.7151 | 74.2989 | 73.3259 | 59.3635 |
| DH50 (100% Ca) | 97.3833 | 72.3686 | 74.8584 | 70.1637 | 61.6743 |
| DH80 (100% Cu) | 97.8611 | 73.0129 | 74.7939 | 70.6768 | 62.7347 |

TABLE 4

Change in chemical shift (ΔHz) of Na pentosan polysulphate (SP54$^R$) ring carbon 13C resonances caused by progressive replacement of Na by Zn, Mg, Ca and Cu

| | ΔHz of Ring C relative to SP54 | | | | |
|---|---|---|---|---|---|
| Compound | 1 | 2 | 3 | 4 | 5 |
| DH40Y (100% Zn) | −8.5320 | +20.7214 | −12.1893 | +28.0310 | +4.8747 |
| DH40J (83% Zn) | −7.3146 | +15.8466 | −8.5320 | +18.2815 | +3.6523 |

TABLE 4-continued

Change in chemical shift (ΔHz) of Na pentosan polysulphate (SP54[R]) ring carbon 13C resonances caused by progressive replacement of Na by Zn, Mg, Ca and Cu

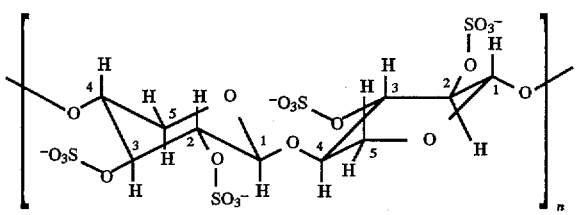

| | ΔHz of Ring C relative to SP54 | | | | |
|---|---|---|---|---|---|
| Compound | 1 | 2 | 3 | 4 | 5 |
| DH40G (8.5% Zn) | 0.0 | +7.3146 | 0 | +8.5320 | +3.6523 |
| DH70 (100% Mg) | −8.5320 | +14.6242 | −12.1893 | +17.0591 | 0 |
| DH50 (100% Ca) | −113.3362 | −52.8355 | +15.8416 | −141.3672 | +115.7711 |
| DH80 (100% Cu) | −89.3984 | −20.3560 | +12.6102 | −115.6609 | +168.8971 | in FIG. 3(A) where electron donation from the sulphate oxygens attached to the 2 and 3' positions of adjacent rings as well as the lone pair electrons on the 1–4 oxygen glycosidic bond and pentose ring oxygen all contribute to the stabilization (Chelation) of the metal complex.

Figure 3B:
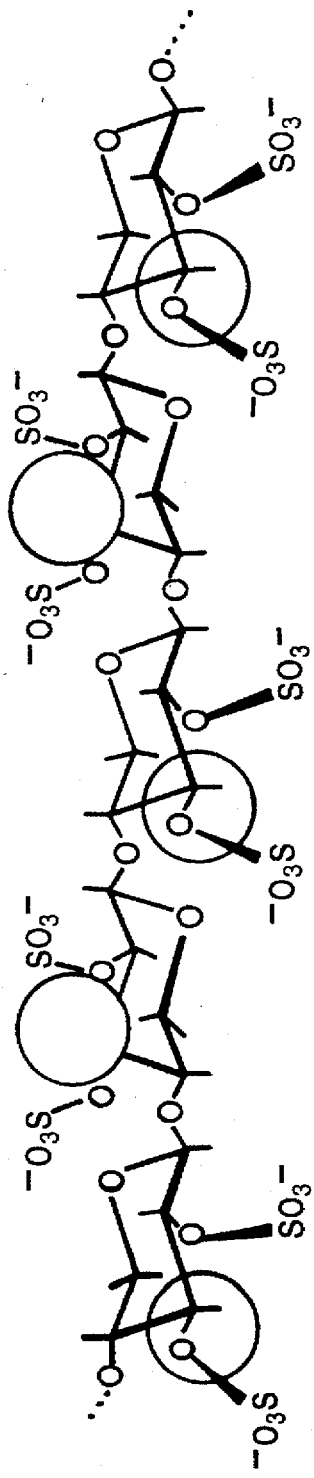

On the other hand, for the calcium and copper complexes with pentosan polysulphate (DH50 and DH80) (Table 4) the penrose ring carbon atoms which were influenced by the metal were quite different. For these metallo complexes, the 1, 2 and 4 carbons were strongly shielded whereas carbons 3 and 5 were deshielded. This indicates that for DH50 and DH80 the metal atoms are tightly located in positions close to the carbons 3 and 5 (opposite side to zinc). Such a situation would occur as shown in FIG. 3(B), and it is contended that for these complexes, sulphate esters in the pentose 2 and 3 positions of the same ring as well as electrons on glycosidic ring oxygen are involved in chelation. Since the spectra of DH50 and DH80 sharpen on raising the temperature, it is concluded that chelation increases with molecular agitation.

It is clearly evident from the data presented in Table 4 and FIG. 3 that the position occupied by the multivalent elements in forming complexes with the sulphated polysaccharides is critically dependent upon the ionic radius of the atom and its electronic configuration. While the conformation and flexibility of the sulphated polysaccharide must also contribute to the stability of the metallo complexes, it is important to note that the present experiments indicate that chelates so formed may have overall preferred conformations which are different to that of monovalent salts (e.g. $Na^+$, $K^+$, $NH_4^+$ etc.).

It is this change of conformation and presentation of functional groups to receptor sites on enzymes and cell surfaces that render the multivalent complexes so different to monovalent species. Examples of such changes are given in the biological activity section.

The binding strength (dissociation constant) of the zinc pentosan polysulphate complexes DH40Y and DH40J relative to sodium (SP54®) was also investigated by $^{13}$C-NMR (Table 5).

Addition of NaCl to a solution of SP54® in water produced an overall decrease in $^{13}$C chemical shift values (Table 5). This arises from a change in conformation of the molecules due to the increased flexibility. As can be seen from Table 5 the most pronounced change occurs at 1.25M NaCl. In contrast the chemical shift changes of DH40Y were much less affected by the addition of NaCl indicating small conformational change in the presence of competing $Na^+$ ions. This suggests that even at 1.25M NaCl the zinc ions were not readily displaced from their sites on the polysulphated polysaccharide.

Biological Properties of the Polysulphated Polysaccharide-Metal Complexes (A) Inhibition of human granulocyte elastase (HGE) by pentosan polysulphate metallo complexes The objectives of these experiments were to determine:

(1) the relative inhibitory activity fo some of the metallo pentosan polysulphate complexes prepared; and (2) to demonstrate that the inhibitory activity produced by these complexes did not result by simply mixing various proportions of pentosan polysulphate sodium salt with zinc ions (see Lukas et al U.S. Pat. No. 4,465,666, EP 12115).

The experiments performed were as follows:

(a) HGE prepared according to the method of Andrews et al (Chem. Biological Int. 47, 157, 1983) was used to degrade

TABLE 5

Influence of sodium chloride on the change in $^{13}$C-chemical shift values ($\Delta$Hz) for the ring carbons of sodium pentosan polysulfate (SP54$^R$) and pentosan polysulfate zinc complexes (DH40 series)

| Compounds | Ring Carbon | Molarity of NaCl | | | | |
|---|---|---|---|---|---|---|
| | | 0.25 | 0.5 | 0.75 | 1.0 | 1.25 |
| SP54$^R$ | 1 | −4.8747 | −6.0922 | −7.3096 | −10.9669 | −13.4068 |
| | 2 | −2.2174 | −7.2174 | −12.4399 | −17.2174 | −21.4399 |
| | 3 | −4.8747 | −8.5320 | −12.1893 | −15.8416 | −20.7164 |
| | 4 | −1.2174 | −4.4399 | −7.2174 | −12.4399 | −15.0654 |
| | 5 | −4.8747 | −4.8747 | −4.8747 | −4.8747 | −6.0972 |
| DH40Y (100% Zn) | 1 | 0 | 0 | −2.4349 | −2.4349 | −7.3096 |
| | 2 | −5.5270 | −9.7495 | −10.9719 | −10.9719 | −12.1893 |
| | 3 | +4.0747 | +2.4399 | 0 | −2.4349 | −4.8747 |
| | 4 | −9.6757 | −13.4068 | −13.4068 | −13.4068 | −12.1893 |
| | 5 | −1.2174 | −3.6573 | −3.6573 | 3.6573 | −4.5240 | the synthetic specific substrate for this enzyme-(succinyl-dialanyl-valyl nitroanalide (SAAVNA)). Inhibition was determined over a range of concentrations and the 50% inhibitory constant (IC$_{50}$) value determined as the concentration of drug (ug/ml) which produced 50% inhibition of 1.0 ug HGE using 0.2 mM phosphate/0.1% BSA/0.0255 Triton X100/5% DMSO pH 7.4 buffer at 37° C.

Figure 5:
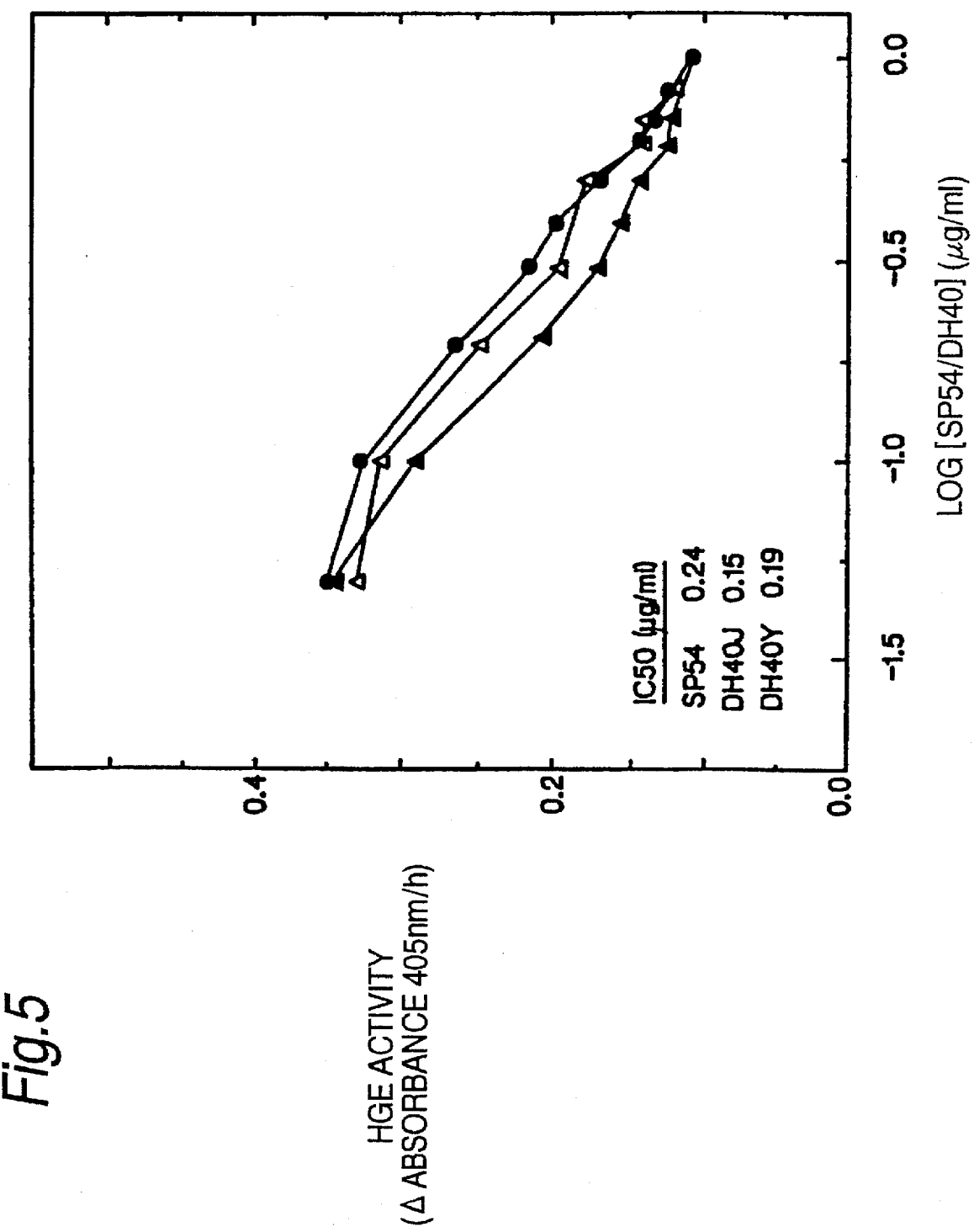
FIG. 5—Inhibition of human granulocyte elastase (HGE) by Pentosan polysulphate (SP54®) (●), DH40J (▲) and DH40Y (Δ). The IC50 (ug/ml) for these three drugs are shown.

Inhibition curves for HGE for SP54®, DH40J, and DH40Y are shown in FIG. 5. As can be seen both zinc complexes were more potent than SP54®. This was also true for DH40G. However, the Cu (DH80), Mg (DH70) and Ca (DH50) pentosan polysulphate complexes were of similar potency to SP54® (Table 6).

This suggests that the conformation adopted by the zinc pentosan polysulphate complexes was capable of interacting more effectively with HGE than SP54®. DH40J was found to be the most potent HGE inhibitor (Table 6).

Figure 6:
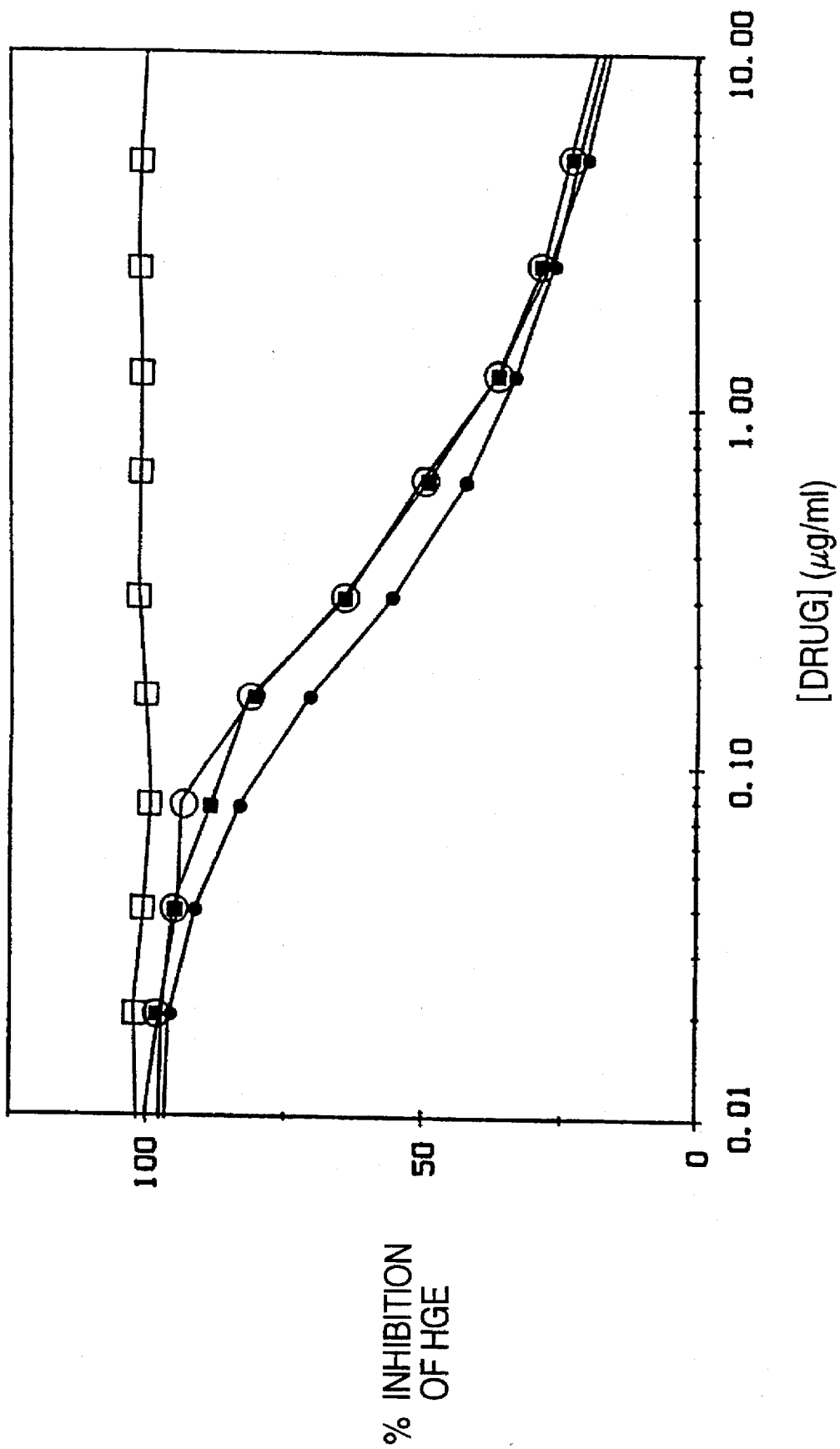
FIG. 6—Inhibition of human granulocyte elastase (HGE) by Pentosan polysulphate (SP54®) (■), DH40J (●), ZnSO$_4$ (□) and ZnSO$_4$+SP54® in the ratio of (1:0:18) (○).

(b) Inhibitory effect of DH40J, pentosan polysulphate (SP54®), zinc sulphate (ZnSO$_4$) and mixtures of (SP54®+ZnSO$_4$) on HGE In these experiments the inhibitory activity of DH40J, PPS as SP54® and mixtures of SP54® and ZnSO$_4$ in various proportions against HGE using the same condition as in (a), except that a different enzyme preparation was used, were investigated. As can be seen from FIG. 6, DH40J was a more potent inhibitor over the concentration range 0.03 ug to 1.0 ug than PPS and PPS+Zn$^{++}$ mixed in the proportions of 1:0.18 which is the approximate ratio of these components in DH40J. A variety of ratios of Zn$^+$ to SP54® were tested for their ability to inhibit the HGE.

As is evident from Table 7 at all ratios examined within the range 1:0.1 to 1:1 the HGE inhibition was not substantially different to SP54® alone, and in no instances comparable to the inhibitory effect produced by DH40J.

TABLE 6

THE INFLUENCE OF CATION CHELATION OF PENTOSAN POLYSULPHATE (SP54) ON INHIBITION OF HUMAN GRANULOCYTE ELASTASE (HGE).

| Code | Cation | IC$_{50}$* (µg/ml) | Comments |
|---|---|---|---|
| SP54 | Na | 0.249 | — |
| OH40(G) | Zn | 0.205 | 8.5% substitution |
| OH40(J) | Zn | 0.158 | 83% substitution # |
| OH40(Y) | Zn | 0.197 | 100% substitution |
| DH50(A) | Ca | 0.232 | — |
| DH60(A) | Ba | — | Insoluble |
| DH70(A) | Mg | 0.223 | — |
| DH80(A) | Cu | 0.249 | — |

*HGE inhibition is expressed as the inhibitor concentration (µg/ml) giving 50% inhibition of 1 µg HGE/ml using 0.2 mM SAAVNA as substrate in 50 mM phosphate/0.1% BSA/0.0255 Triton X100/5% DMSO pH 7.4 at 37° C. #DH40(J) is the most potent HGE inhibitor.

TABLE 7

EFFECT OF DH40, SP54, ZINC SULPHATE AND SP54 + ZINC SULPHATE ON THE INHIBITION OF HUMAN GRANULOCYTE ELASTASE (HGE)

| INHIBITOR | RATIO SP54: zinc ions by weight | IC$_{50}$ (µg/ml) | % DIFFERENCE from SP54 |
|---|---|---|---|
| SP54 | — | 0.381 | 0 |
| SP54 + Zn$^{++}$ | 1:0.1 | 0.353 | −7 |
| | 1:0.18 | 0.389 | +2 |
| | 1:0.2 | 0.353 | −7 |
| | 1:0.3 | 0.353 | −7 |
| | 1:0.4 | 0.381 | 0 |
| | 1:0.6 | 0.381 | 0 |
| | 1:1 | 0.411 | +8 |
| DH40J | 1:0.18 | 0.246 | −35 |
| ZnSO$_4$ | — | 10 | — |

Figure 7:
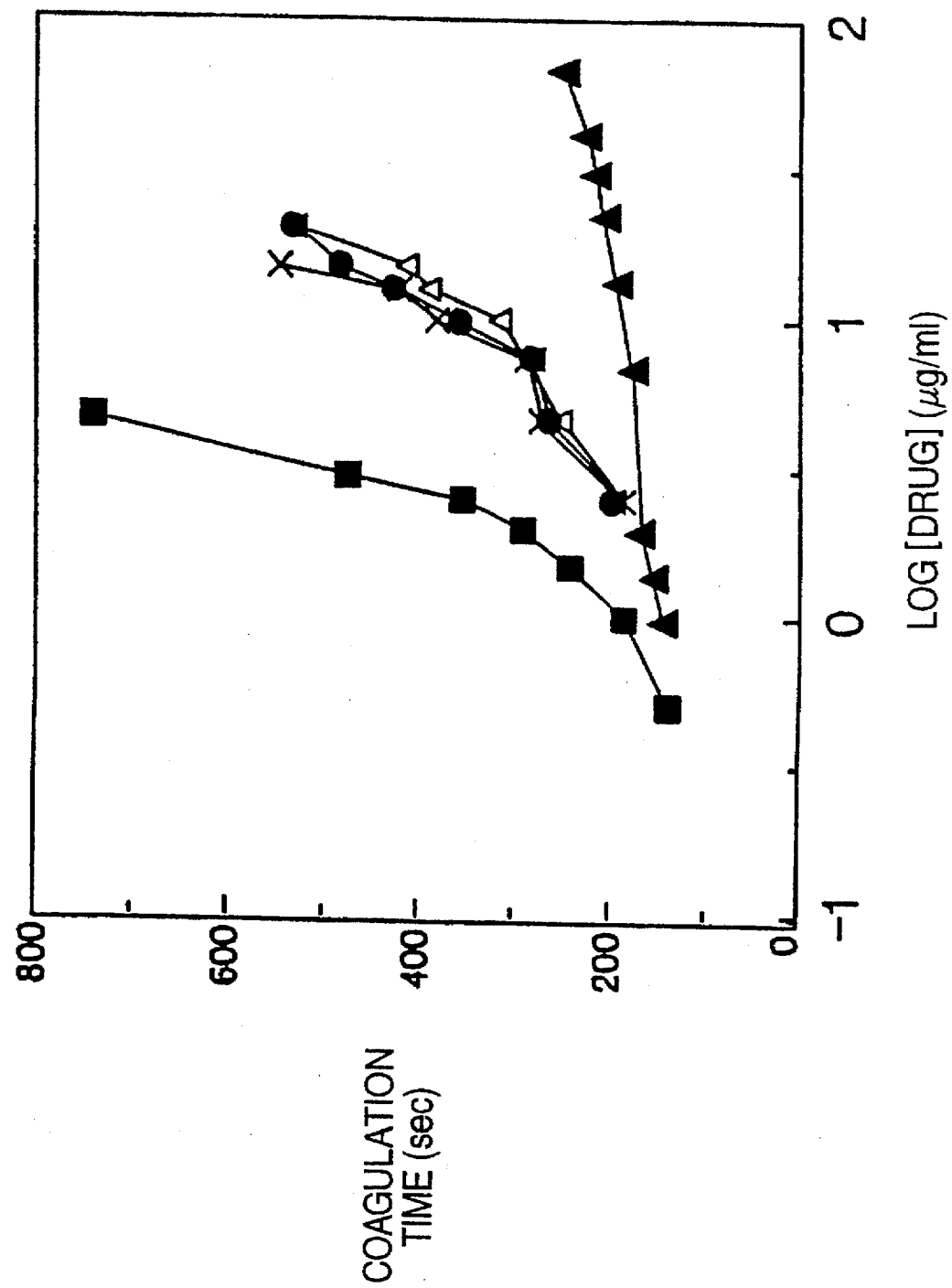
FIG. 7—Anticoagulant effect of Heparin (■) Pentosan polysulphate (SP54®) (●), DH40J (▲), DH50 (Δ) and DH80 (X) against guinea pig plasma.
Figure 8:
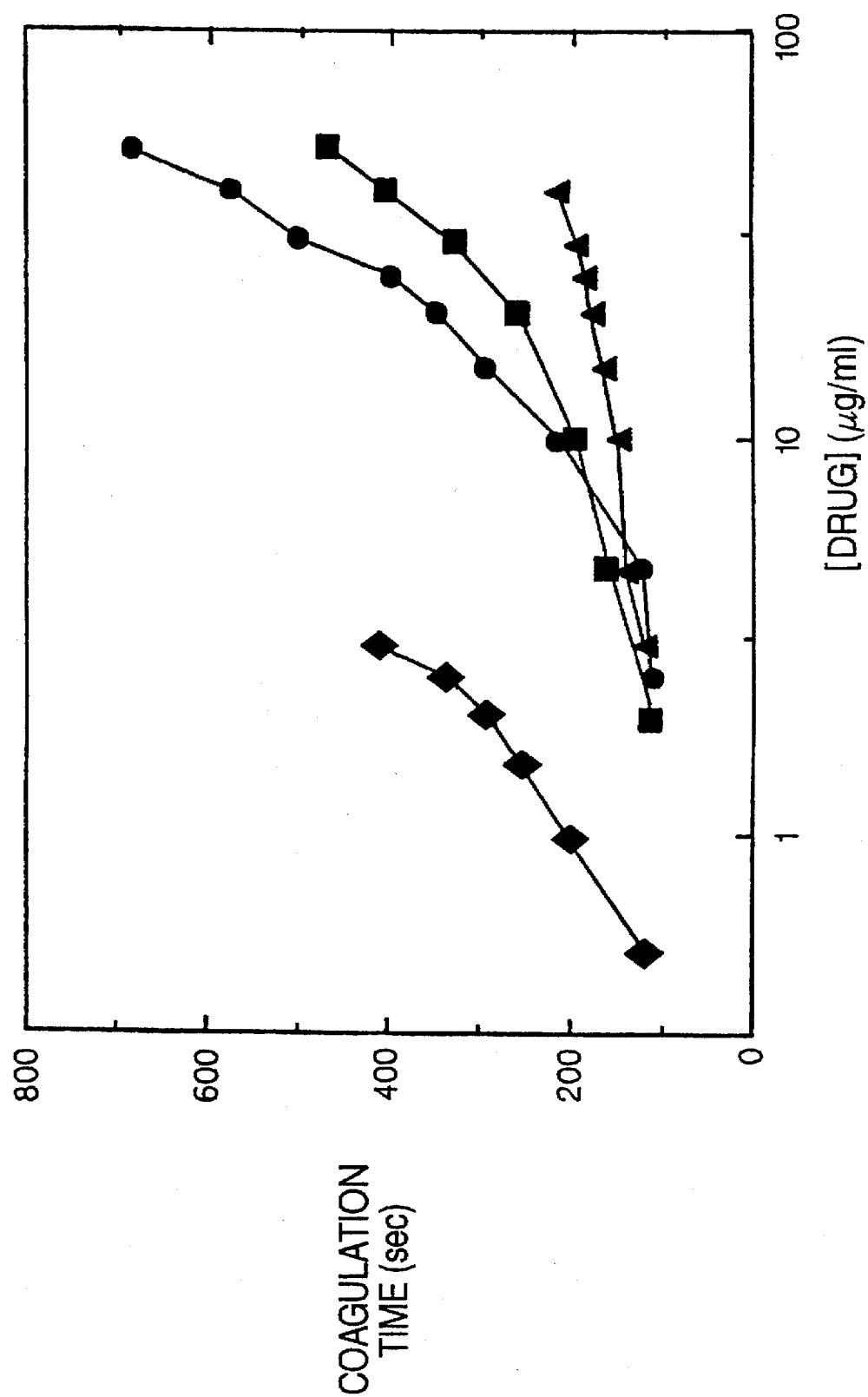
FIG. 8—Anticoagulant ability of Heparin (♦), Pentosan polysulphate (SP54®) (●), DH40G (■) and DH40J (▲) against guinea pig plasma.

(B) Effects of pentosan polysulphate-metallo complexes on the blood coagulation pathways Pentosan polysulphate (SP54®) is a potent inhibitor of coagulation and is sold commercially as a "synthetic heparin" i.e. a heparinoid. A major gaol for the present investigations was to alter the conformation of the polysulphated polysaccharides to reduce the anticoagulant ability of these macromolecules but maintain their other biological properties. As is evident from FIG. 7, this was successfully achieved from the zinc polysulphated polysaccharides as exemplified by the DH40 series where progressive replacement of Na$^+$ by zinc to form the complex reduced anticoagulant activity. Since the calcium (DH50) and copper (DH80) pentosan polysulphate complexes were equipotent with the unsubstituted parent sodium salt it must be assumed that the conformation adopted by the $Ca^{++}$ and $Cu^{++}$ complexes (see FIG. 8) was still able to interact with serine proteinase of the coagulation cascade.

Figure 9A:
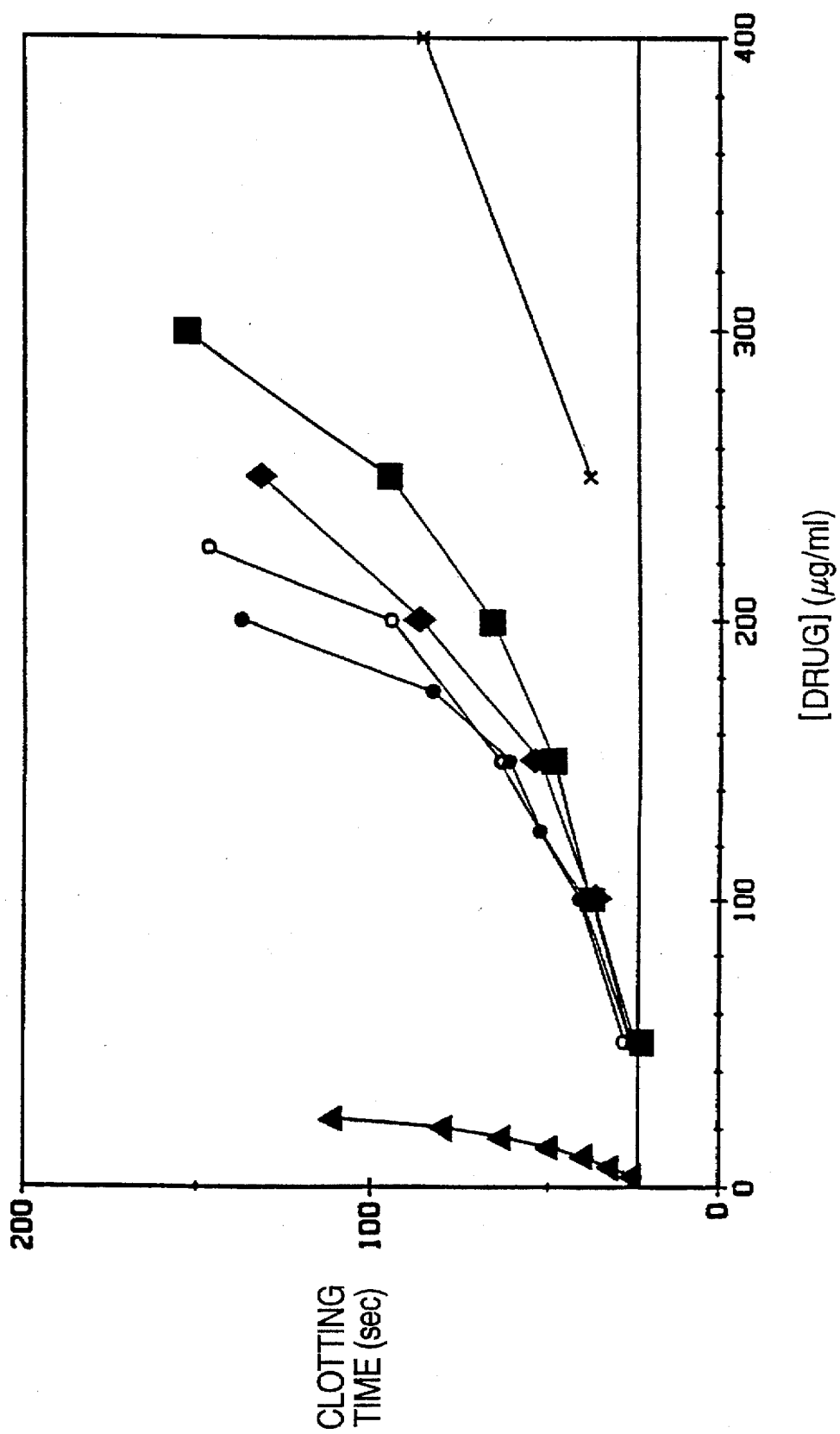
FIG. 9A—Effect of Heparin (▲), SP54® (●), SP54®+Zn$^{++}$ in the ratio (1:0.176) or (1:0.22) (○) DH40J (♦) DH40Y (■) or ZnSO$_4$ (X) on the prothrombin time of normal human plasma.
Figure 9B:
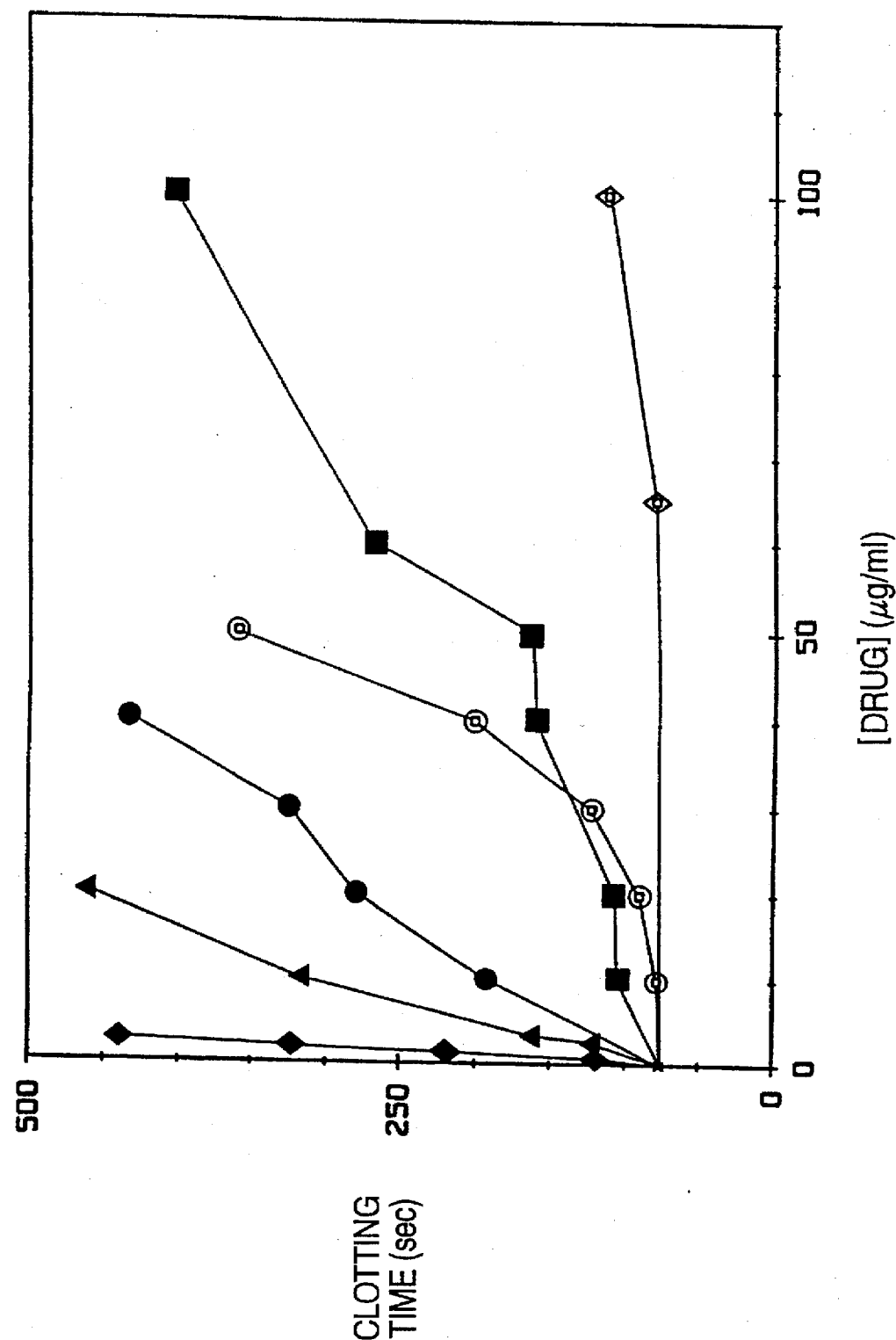
FIG. 9B—Anticoagulant effect of Heparin (♦) Pentosan polysulphate (SP54®) (▲), Dextran polysulphate (DS5000) (●), Dextran polysulphate (DS5000)+ZnSO$_4$ in the ratio of (1:0.47) (◉), Dextran polysulphate (DS5000) -Zn chelate complex (■) and ZnSO$_4$ (◆) against guinea pig plasma.

In order to confirm that the unique biological activity induced in the polysulphated polysaccharides was due to the compounds synthesised and could not be reproduced by simply mixing $Zn^{++}$ and a polysulphated polysaccharide in solution various mixtures were made and tested as anticoagulents. As can be seen from FIG. 9A, DH40J and DH40Y showed reduced anticoagulant activity relative to SP54 as determined by prothrombin time using normal human plasma. Significantly solutions made from $Z^{++}$ and SP54 in the same proportion as in DH40J (0.176:1) and DH40Y (0.22:1) were similar to SP54, but quite different to DH40J and DM40Y. Similar results were obtained for the corresponding zinc-dextran polysulphate complexes (see FIG. 9B).

Figure 10:
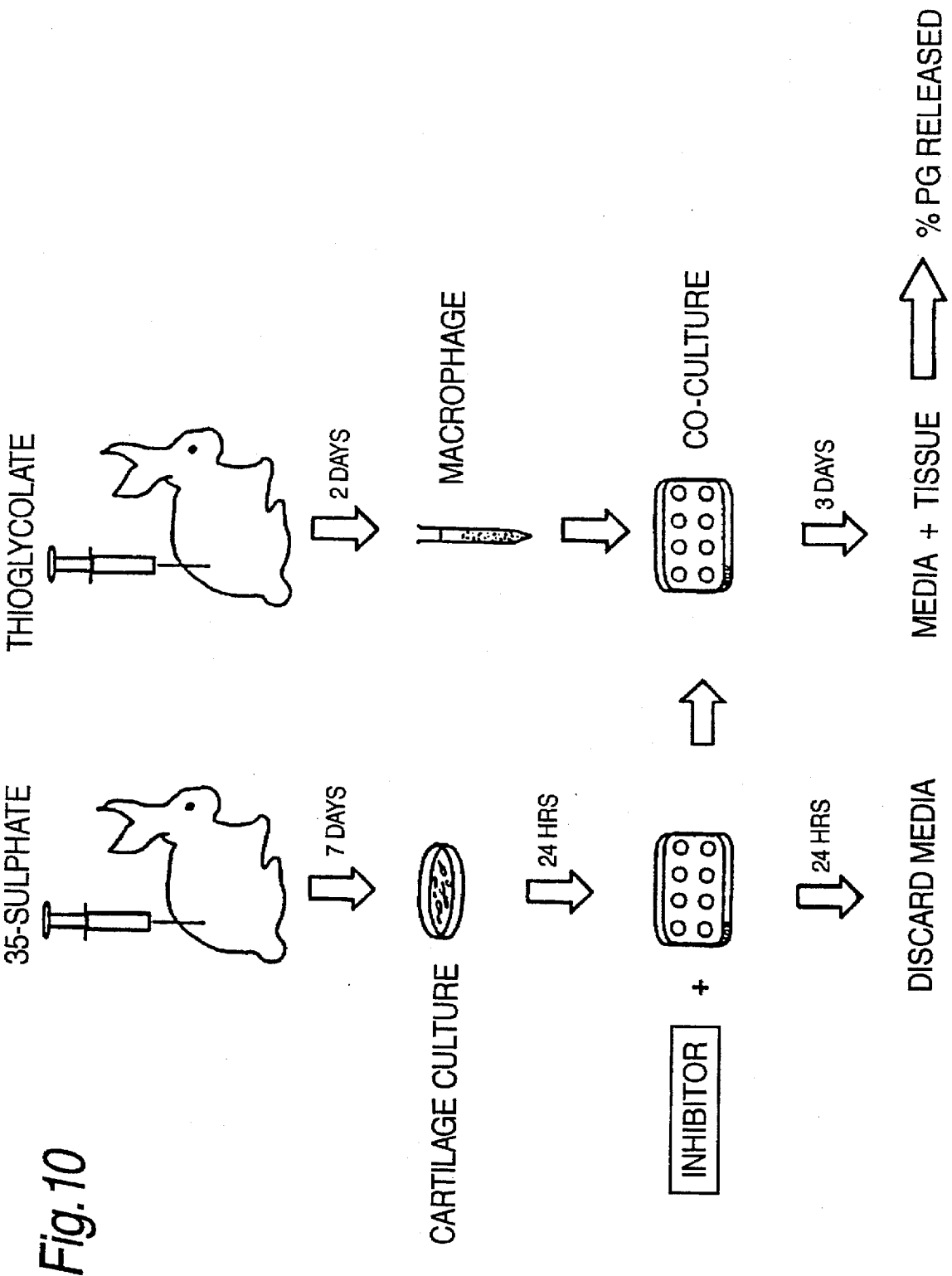
FIG. 10—Schematic representation of the methods used to evaluate the inhibitory effects of drugs on IL-1 (in macrophage supernatants) mediated degradation of cartilage in vitro. $^{35}$-Sulphate was used to radiolabel proteoglycans in rabbit joint articular cartilage. Thioglycolate was used to stimulate accumulation of activated macrophage in rabbit peritoneal cavity.
Figure 11:
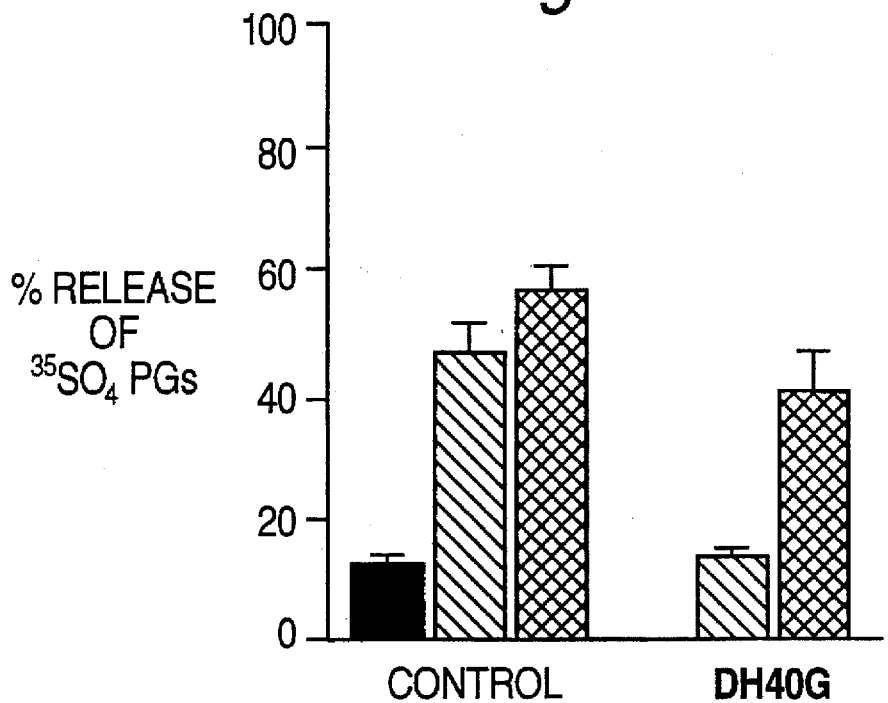
FIG. 11—Effects of DH40G or saline control on the IL-1 mediated degradation of rabbit cartilage in vitro. In the control groups.

(C) Effects of DH40G on the IL-1 Mediated Degradation of Cartilage In-Vitro (FIGS. 10 and 11)

Fell and Jubb [Arthritis & Rheum. 20, 1359, (1977)] using co-cultures of cartilage and synovial tissue explants were the first to report that a factor from the synovium caused chondrocytes to degrade their own cartilage matrix. This factor was called "Catabolin" and subsequently was purified by Saklavala and co-workers [Biochem. J. 199, 705, (1981)] and shown to belong to the interleukin-1 or IL-1 family of monokines. It has also been shown that the synovial type A cells of the synovial lining are bona fide macrophages. It is easy to envisage some event or situation arising within the joint in which the joint synovial cells may become stimulated, even very marginally, to produce IL-1. Interleukin-1 has been detected in synovial fluid of inflamed joints. A small output of IL-1 above normal levels, perfusing cartilage, could therefore with time, result in a disturbance in the metabolism of articular cartilage with the loss of PGs from the matrix occurring as an early event. This could lead ultimately to eroded and degenerate cartilage and the classical pathology of osteoarthritis.

An in-vitro model was therefore developed on the assumption that IL-1-mediated autolysis of articular cartilage was an important component of the pathology of osteoarthritis.

Slices of rabbit knee articular cartilage, pre-labelled in-vivo with $^{35}SO_4$, were co-cultured with macrophages, conveniently obtained from the peritoneum. The macrophages produce IL-1 which stimulates the chondrocytes to degrade their matrix, releasing $^{35}SO_4$ labelled GAGs into the culture medium. Potential anti-arthritic drugs, such as the DH40 were tested using this model for any propensity to inhibit IL-1-mediated cartilage degeneration. FIG. 10 illustrates the principle of the method used.

Methods

New Zealand white rabbits, 6–8 weeks old, were injected intramuscularly with 3mCi $H_2\ ^{35}SO_4$ a week before sacrifice. Similar animals were injected intraperitoneally with 25 ml thioglycollate medium, to recruit macrophages, 48 hours before sacrifice. In a typical experiment, the cartilage donor was killed and cartilage from the knee joint, including the patella, was shaved off with a #11 scapel blade. The resulting explants, which were variable in size, were cultured for 3 days in Ham's F12 medium containing 10% FCS. The explants were then washed twice with serum-free medium and transferred individually to wells of 24-well tissue culture plates. On the same day, the macrophage donor was killed and macrophages collected by peritoneal washing and centrifugation. The test compounds were added to the appropriate wells and finally $5 \times 10^4$ macrophages were added per well. The final volume was 250 ul of serum-free Ham's F12 medium per well. After 3 days incubation the cultures were terminated. The supernatants were collected and the wells were rinsed with 200 ul of saline which were added to the supernatant. The counts per minute of $^{35}SO_4$-labelled proteoglycans in these samples represented the PGs lost from the cartilage matrix due to degradation. The explants themselves were solubilised by papain digestion and an aliquot of each was counted to record the undegraded PGs still retained within the cartilage matrix.

Results

The results of a typical experiment are shown in FIG. 11, where it can be seen that DH40 was effective in suppressing the IL-1 mediated loss of PGs from articular cartilage when either used directly (Macrophage conditioned media, MCM, or when co-cultured with peritoneal exudate cells (PEC).

(D) Studies of the relative effects of DM40G and Pentosan polysulphate (SP54) on the loss of proteoglycans from cartilage in an experimental model of arthritis Introduction This model was originally described by Sin, M. Y., et al J. Path. 141, 23 (1984) and Sedgwick A. D. et al Ann. Rheum. Dis. 43, 418 (1984) and provides a convenient and reproducable method of evaluating the effects of drugs on cartilage metabolism in vivo. This model was used to investigate the influence of SP54® and DH40J when administered into the rat air pouch at 10 mg/kg on the loss of cartilage proteoglycans (PGs) induced by an inflammatory cell invasion of the pouch.

Materials and Methods

Air pouches were created on the dorsal surface of male 200 gm Wistar rats by the initial injection of 20 ml of sterile air. Re-injection every second day maintained cavity inflation. Articular cartilage (AC) aseptically harvested from the knee joints of 10 week old New Zealand White rabbits, was implanted into formed 7 day old rat air pouches. Drugs (10 mg/kg), diluted in saline, were administered daily into the air pouch beginning the day of cartilage implantation. Saline was administered to a control group. Inflammation of the air pouch was achieved by the injection of 10 ml of sterile 3% peptone into the pouch every second day, beginning the day of cartilage implantation. Animals were killed 7 days later and air pouch fluid (APF) and AC were collected for analysis. Cells in the APF were stained with crystal violet and a total cell count determined. A differential cell count was perfomed by cytocentrifugation and staining with giemsa. Implanted AC (8–10 mgs) was digested by papain and PG content was determined by hexuronic acid and sulphated glycosaminoglycan (GAG) analysis. PGs in the remaining AC were extracted with 4M GuHCl plus protease enzyme inhibitors. Extractability of PGs and their ability to aggregate with exogenous hyaluronic acid (HA) 20%) was determined by chromatography on Sepharose CL-2B. A portion of AC surface was examined by S.E.M. following dehydration of the speciment in the graded acetone, critical point drying and gold coating.

Results

Both SP54® and DH40G appeared to be equally effective in preventing the loss of proteoglycans from implanted articular cartilage in this pouch model. Briefly however it was found that the DH40G prevented loss of proteoglycans (PGs) (as measured by uronic acid) (FIG. 12), maintained PG extractability (FIG. 13) and aggregation (FIG. 14) of cartilage implanted into the pouch where inflammatory cell numbers were high. Some indication of the mechanism of action of these drugs was provided by histological examination of the cartilages removed from the pouch. It was found that the number of inflammatory cells adhering to cartilage of drug treated speciments was considerably less than control cartilages. Since enzymes and mediators of cartilage destruction are released by the inflammatory cells into cartilage the suppression of their number at the cartilage surface must be considered as a direct beneficial effect.

(E) Effects of Pentosan polysulphate (PPS) DH40J, $ZnSO_4$ and $ZnSO_4$ +PPS on DNA synthesis by a human synovial fibroblast line in vito Repair of connective tissue, including cartilage in osteoarthritis (OA), requires DNA synthesis and proliferation (mitosis) of cells within the tissue matrix. Many non-steroidal anti-inflammatory drugs (NSAIDs) and corticosteroids suppress this important cellular process and can impair recovery. Complexation of the pentosan polysulphate with the multivalent metals was found to stimulate DNA synthesis over a very low concentration range of the drugs.

As is evident from FIG. 15 at concentrations up to 100 ug/ml DH40J stimulated the in vitro biosynthesis of DNA in synovial fibroblasts derived from OA joints to a greater extent than PPS (SP54®). Moreover as with all other experiments tried, solutions containing zinc ions and the pentosan polysulphate in proportions comparable to that which exist in the prepared metallo polysulphated complexes failed to reproduce this powerful effect on cell macromolecular synthesis.

(F) Effects of SP54®, DH40J and DH40Y on proteoglycan biosynthesis by rabbit articular chondrocyte As discussed above, in chronic OA and allied conditions, the extracellular matrix is subjected to excessive catabolism. Tissue cells need to replicate and produce a new matrix to survive and maintain functionality. While many drugs including antiinflammatory agents may suppress this process it is known (Burkhardt & Ghosh Seminars in Arthritis & Rheumatism 17, Suppl. 1 3–34, 1987) that the polysulphated polysaccharides do not. It was of some interest, therefore, to find that the metallo complexes of this class of drugs were more potent stimulators of proteoglycan synthesis than the sodium salt. The results for SP54® DH40J, and DH40Y are shown as an example (see FIG. 16).

The use of polysulphated polysaccharides and the metallo polysulphate polysaccharides in combination with corticosteriods to ABROGATE the inhibitory effects of the latter on cell mitosis and macro molecular Biosynthesis Corticosteroids are known to suppress connective tissue cell mitosis and biosynthesis of matrix components, e.g. collagen, proteoglycans and hyaluronic acid (HA). these macromolecules are essential for normal bodily functions and health.

In this study it was shown that SP54® and to a greater extent DH40J could prevent the deleterious effects of hydrocortisone on in vitro synovial fibroblast biosynthesis of hyaluronic acid (HA). The results obtained are summarized in the following figures.

FIG. 17—shows with increasing concentration of hydrocortisone, HA biosynthesis is progressively inhibited.

FIG. 18—shows concentration effects of DH40J on HA biosynthesis by synovial fibroblasts.

FIG. 9—shows partial restoration of HA synthesis by synovial fibroblasts by SP54 when cells exposed to hydrocortisone at $10^{-6}M$.

FIG. 20—shows complete restoration to control values produced by SP54 when the concentration of hydrocortisone used was reduced to $1\times10^{-8}M$.

FIG. 21—as for FIG. 20 but DH40J used instead, hydrocortisone $10^{-6}M$.

FIG. 22—as for FIG. 20 but DH40 used instead, hydrocortisone at $10^{-8}M$.

Anti-viral Activity

1. Activity Against Human Immunodeficiency Virus (HIV) and Friend Leukemia Virus (FLV)

Different chelates of pentosan polysulphate were tested in vitro against HIV-1 in a human lymphocyte culture system and against FLV in vivo in a mouse model. The various chelates of pentosan polysulphate used are set out in Table 8.

TABLE 8

| Pentosan Polysulphate Compounds Tested | |
|---|---|
| ZnPPS-A | = pentosan polysulphate Zinc chelate (5.63% Zn) |
| ZnPPS-B | = pentosan polysulphate Zinc chelate (12.68% Zn) |
| ZnPPS-C | = pentosan polysulphate Zinc chelate (13.9% Zn) |
| ZnPPS-D* | = pentosan polysulphate Zinc chelate (14.97% Zn) |
| ZnPPS-E* | = pentosan polysulphate Zinc chelate (15.3% Zn) |
| CaPPS | = pentosan polysulphate Calcium chelate (10.44% Ca) |
| MgPPS | = pentosan polysulphate Magnesium chelate (5.88% Mg) |

*two different batches

Methods

Cells

Peripheral blood mononuclear cells (PBL) from healthy HIV-sero-negative volunteers were obtained by Ficoll-Hypaque sedimentation of citrate-containing blood. Cells were stimulated with phythaemagglutinin (PHA) and grown in RPMI-1640 cell culture medium (Biochrom) supplemented with 10% fetal calf serum (FCS). After 2 or 3 days of exposure to PPHA the cells were washed 3 times, cells were frozen and stored under liquid nitrogen until required.

Anti-HIV Assay

Thawed PBL were cultured in RPMI-1640 medium containing 10% FCS and recombinant interleukin-2 (10 IU/ml, Roussel Uclaf, France) for 4 days before they were infected for a 30 minute period with HIV (approx. $2-4\times10^5$ TCIU/ $1\times10^6$ cells).

The virus-containing supernatent was removed, the infected PBL were transferred to 24-well plates; test compounds were added immediately (end concentration of cells; $2.5\times10^5$ cells/ml/well). Seventy-two hours after incubation of the cell cultures in a $CO_2$ (5%) air (95%) incubator virus replication was evaluated by light microscopy for syncytia formation.

In this and subsequent assays all test compounds were dissolved in DMSO at the following concentrations of 37.5 µg/ml; 75 µg/ml; 150 µg/ml and 300 µg/ml.

FLV Assay

Groups of ten female NMRI mice were infected intravenously with 0..2 ml of a 1:5000 diluted mouse serum containing Friend Leukemia Virus. Intraperitoneal administration of the drugs was started 48 hours after infection for a period of 10 days 2 times daily (20 doses). Fourteen days after infection, the animals were killed by cervical dislocation and the spleens were removed from the animals. The weight of the spleens served as a parameter for the virus replication.

Results

HIV Assay: The minimal inhibiting concentrations obtained for each of the chelates is set out in Table 9. From these results, it is evident that all of the chelates tested are active against HIV.

FLV Assay: The results that are set out in Table 10 show that all chelates tested were active. Because of significantly greater activity of ZnPPS-E and CaPPS, these compounds were tested in a second experiment, the results of which are shown in Table 10. Due to the high activity again obtained for CaPPS, this compound was tested in a third experiment, the results of which are shown in Table 10.

TABLE 9

Inhibitory activity of Different Pentosan Polysulphate Chelates Against HIV-1 in the Lymphocyte System

| | MIC (µg/ml)** |
|---|---|
| ZnPPS-A | 4 |
| ZnPPS-B | 20 |
| ZnPPS-C | 4 |
| ZnPPS-D* | 20 |
| ZnPPS-E* | 20 |
| CaPPS | 4 |
| MgPPS | 20 |

*only partially dissolved
**MIC = minimal inhibitory concentration

TABLE 10

Effect of Treatment with Different Pentosan Polysulphate Chelates on FLV Infection in Mice

| Compound | Cumulative Dose (mg/kg) | Spleen Weight | Survivors/ total | p*(values) |
|---|---|---|---|---|
| Experiment 1: | | | | |
| Control (no drug) | 20 × 0 | 1.77 ± 0.54 | 10/10 | 1.0000 |
| ZnPPS-A | 20 × 4.15 | 1.73 ± 0.28 | 7/10 | 0.4572 |
| | 20 × 12.50 | 1.73 ± 0.50 | 9/10 | 0.4947 |
| ZnPPS-B | 20 × 4.15 | 2.17 ± 0.59 | 9/10 | 0.0253 |
| | 20 × 12.50 | 1.69 ± 0.40 | 10/10 | 0.4798 |
| ZnPPS-C | 20 × 4.15 | 1.68 ± 0.47 | 10/10 | 0.2504 |
| | 20 × 12.50 | 1.89 ± 0.23 | 9/10 | 0.2713 |
| ZnPPS-D | 20 × 4.15 | 1.72 ± 0.67 | 8/10 | 0.4405 |
| | 20 × 12.50 | 1.88 ± 0.37 | 10/10 | 0.3050 |
| ZnPPS-E | 20 × 4.15 | 1.37 ± 0.83 | 8/10 | 0.0180 |
| | 20 × 12.50 | 1.61 ± 0.47 | 10/10 | 0.0259 |
| CaPPS | 20 × 4.15 | 1.14 ± 0.55 | 10/10 | 0.0024 |
| | 20 × 12.50 | 1.37 ± 0.42 | 10/10 | 0.0146 |
| MgPPS | 20 × 4.15 | 1.59 ± 0.36 | 10/10 | 0.2686 |
| | 20 × 12.50 | 1.55 ± 0.34 | 10/10 | 0.1998 |
| Experiment 2: | | | | |
| ZnPPS-E | 20 × 4.15 | 1.79 ± 0.44 | 10/10 | 0.0020 |
| | 20 × 12.50 | 2.02 ± 0.44 | 10/10 | 0.0067 |
| CaPPS | 20 × 4.15 | 1.86 ± 0.58 | 10/10 | 0.0138 |
| | 20 × 12.50 | 1.46 ± 0.37 | 8/10 | 0.0001 |
| Experiment 3: | | | | |
| Control (no drug) | 20 × 0 | 1.77 ± 0.54 | 10/10 | 1.0000 |
| CaPPS | 20 × 6.25 | 1.39 ± 0.42 | 8/10 | 0.0459 |
| | 20 × 12.50 | 1.42 ± 0.64 | 5.10 | 0.0788 | not infected controls (not determined in this experiment) <0.2
*compared with non drug treated controls 2. Activity Against Herpes Simplex Type 2 Virus The zinc chelate of pentosan polysulphate ZnPPS-E (15.3% Zn) was tested for anti-viral activity against Herpes Simplex Type 2 Virus.

Methods

A. Preparation of Organisms

Herpes simplex type 2 virus was used for the study. A viral suspension was prepared by growing the virus in a cell culture and removing the gross debris by low speed centrifugation (3000rom for 10 mins). The resulting supernatent was used in the testing. The supernatent contained approximately $10^4$ viable viral particles per ml (normal clinical conc.).

B. Preparation of Sample

The test sample was diluted with cell culture medium to concentrations of 1 mg/ml, 50, 10, 1 and 0.1 µg/ml.

C. Procedure

One ml of each of the above solutions was mixed with 100 $ID_{50}$ of Herpes simplex type 2 virus, allowed to stand at room temperature for 30 minutes, and then added to human fibroblast cell cultures. Tests were carried out in triplicate. A single set of familiar dilutions was made and inoculated into fibroblast cultures without the addition of virus to determine any visible evidence of toxicity.

A second set of tests was carried out using concentrations of 20, 10, 7.5 and 2.5 µg/ml, and using similar methods to those described above.

Results

The virus was found to be inactivated at 10 µg/ml but not at 1 µg//ml or 0.1 µg/ml.

In the second set of tests, the virus was inactivated0 (did not multiply) at concentrations of 10, 7.5, 5 and 2.5 µg/ml but was unaffected by the 1 µg/ml sample.

3. Activity Against herpes Simplex Type 1 Virus (HSV-1)

The calcium chelate of pentosan polysulphate (10.4% Ca) was tested against HSV-1 to determine the 50% inhibitory. concentration for that compound ($IC_{50}$).

HSV-1, strain 44088 was a clinical isolate identified by specific monoclonal antibodies.

Indicator cells used were MRC-S.

Test samples were diluted in minimal essential medium in 10-fold increments from 10 mg/mL to 1 mg/mL. An equal volume of 100 $TCID_{50}$ of HSV-1 was added to the diluted samples and allowed to react at room temperature for 30 minutes. MRC-5 cells were then added and the microplate covered and incubated at 37° in a $CO_2$ incubator for 6 days. The tests were set up in quadruplicate and cytotoxicity controls in duplicate. Cell control and virus back-titration were included in the experiments.

Cells were examined for cytotoxicity and viral cytopathic effect for up to 6 days.

Dilutions of the samples exhibiting cytotoxic effect were excluded from the $IC_{50}$ calculation and are reported separately.

The $IC_{50}$ was calculated for each salt using the method of Reed and Muench and taking into account the additional two-fold dilution with virus.

The experiment was repeated on two occasions.

Results

In both experiments, the $IC_{50}$ of the Ca chelate of PPS against HSV-1 was found to be 50 µg/ml.

Based on the experimental work set out above, the applicants believe that the chelates of this invention clearly demonstrate anti-viral activity. In particular it is shown that the chelates are active against enveloped viruses as exemplified by Herpes Simplex and slow viruses as exemplified by Human Immunodeficiency virus.

Although reference has been made to the utility of the compounds of the invention in treating osteoarthritis and rheumatoid arthritis, other disease states that could be usefully treated include, bursonitis, tendonitis, tendovaginitis and related soft tissue inflammation; wounds and the healing of burns; skin repair, acne and other dermatological acute disorders; topical application for superficial thrombosis, haematoma, ulcus crusis, softening of scars; pancreatis, emphysema and bacterial invasion where excess proteolytic activity occurs.

We claim:

1. A method of treating an infection in a host infected by a virus selected from the group consisting of Friend Leukemia Virus, Herpes Simplex Type 1 and Herpes Simplex Type 2, comprising the step of administering to said host an effective amount of a pure divalent metal ion chelate of a polysulfate of xylan having glycosidically linked D-glucuronyl side chains with divalent metal ions chelated thereto wherein substantially all monovalent ions have been substituted by divalent metal ions being selected from the group consisting of $Ca^{2+}$, $Mg^{2+}$, $Cu^{2+}$ and $Zn^{2+}$.

2. A method according to claim 1, wherein the metal ion is $Cu^{2+}$ or $Zn^{2+}$.

3. A method according to claim 1, wherein the metal ion is $Ca^{2+}$ or $Mg^{2+}$.

4. A method according to claim 2, wherein the xylan polysulfate has an average molecular weight of 6,000 Daltons and a sulphur content of about 16%.

5. A method according to claim 3, wherein the xylan polysulfate has an average molecular weight of 6,000 Daltons and a sulphur content of 16%.

6. A method according to claim 5, wherein the metal ion is $Ca^{2+}$.

* * * * *